US006300124B1

(12) United States Patent
Blumenfeld et al.

(10) Patent No.: US 6,300,124 B1
(45) **Date of Patent: *Oct. 9, 2001**

(54) DEVICE AND METHOD TO DIRECTLY CONTROL THE TEMPERATURE OF MICROSCOPE SLIDES

(75) Inventors: Martin Blumenfeld, Minneapolis; Avram Bar-Cohen, St. Louis Park; Gregory T. Cibuzar, Eagan; Peter Schiller, Coon Rapids; Mehmet Arik, St. Paul, all of MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/432,012

(22) Filed: Nov. 2, 1999

(51) Int. Cl.[7] ............................ C12M 1/34; C12M 1/36; C12M 1/38; C12M 3/00; C12P 19/34

(52) U.S. Cl. .................................... 435/287.2; 435/283.1; 435/287.1; 435/286.1; 435/286.2; 435/91.2; 435/91.1

(58) Field of Search ............................ 435/6, 91.1, 91.2, 435/183, 283.1, 286.1, 287.1, 287.2, 288.4; 436/94; 536/23.1, 24.3, 24.33

(56) References Cited

U.S. PATENT DOCUMENTS

| | | | |
|---|---|---|---|
| 4,013,038 | 3/1977 | Rogers et al. | 118/5 |
| 4,043,292 | 8/1977 | Rogers et al. | 118/5 |
| 4,384,193 | 5/1983 | Kledzik et al. | 219/521 |
| 4,561,961 | 12/1985 | Hofmann | 204/299 R |
| 4,674,846 | 6/1987 | Lippman | 350/536 |
| 5,455,175 | 10/1995 | Wittwer et al. | 435/286.1 |
| 5,475,610 | 12/1995 | Atwood et al. | 364/500 |
| 5,498,392 | 3/1996 | Wilding et al. | 422/68.1 |
| 5,504,007 | 4/1996 | Haynes | 435/285.1 |
| 5,525,300 | 6/1996 | Danssaert et al. | 422/99 |
| 5,527,510 | 6/1996 | Atwood et al. | 422/104 |
| 5,538,871 | 7/1996 | Nuovo et al. | 435/91.2 |
| 5,681,111 | 10/1997 | Akbar et al. | 374/185 |
| 6,074,868 * | 6/2000 | Blumenfeld et al. | 435/286.1 |

FOREIGN PATENT DOCUMENTS

| | | | |
|---|---|---|---|
| 0603411 | 6/1994 | (EP) | C12M/1/38 |
| 93/19207 | 9/1993 | (WO) | C12Q/3/00 |

OTHER PUBLICATIONS

Lowndes et al., A versatile light microscope heating stage for biological temperatures. J. Microscopy 142, 371–374, Jun. 1986.*

Friedman et al., Capillary Tube resistive thermal cycling. Anal. Chem. 70, 2997–3002, 1997, Jul. 1998.*

Abstract of PCT Patent No. WO94/01529 (Katoh K.) Issued Jan. 20, 1994, Filed Jun. 28, 1993, 2 p.

* cited by examiner

*Primary Examiner*—Ethan Whisenant
*Assistant Examiner*—Frank Lu
(74) *Attorney, Agent, or Firm*—Westman, Champlin & Kelly, P.A.

(57) ABSTRACT

A thermal cycling device for use with self-heating microscope slides is provided.

39 Claims, 9 Drawing Sheets

DEVICE AND METHOD TO DIRECTLY CONTROL THE TEMPERATURE OF MICROSCOPE SLIDES

BACKGROUND OF THE INVENTION

The polymerase chain reaction (PCR) is a technique involving multiple cycles that results in the geometric amplification of specific polynucleotide sequences present in a test sample each time a cycle is completed. To amplify the specific nucleic acid sequences ("target sequences"), PCR reagents are combined with the test sample. These reagents include, for example, an aqueous buffer, pH 8–9 at room temperature, usually also containing approximately 0.05 M KCl; all four common nucleoside triphosphates (e.g., for DNA polymerase, the four common dNTPs: dATP, dTTP, dCTP, and dGTP) at concentrations of approximately $10^{-5}$ M to $10^{-3}$ M; a magnesium compound, usually $MgCl_2$, generally at a concentration of about 1 to 5 mM; a polynucleotide polymerase, preferably a thermostable DNA polymerase, e.g., the DNA polymerase I from Thermus aquaticus, at a concentration of about $10^{-10}$ to $10^{-8}$ M; and single-stranded oligonucleotide primers, preferably deoxyribo-oligonucleotides, usually 15 to 30 nucleotides in length, containing base sequences which have Watson-Crick complementarity to sequences preferably on each strand of the target sequence(s). Each primer is present at a concentration of about $10^{-7}$ to $10^{-5}$ M.

Initially, a reaction tube containing the test sample is heated to a temperature at which nucleic acid sequences are denatured, generally 90° C. to 100° C. Then the sample is subjected to a temperature at which oligonucleotide primers, preferably at least two oligonucleotide primers, can anneal to opposing strands of the target sequence, generally 40° C. to 75° C. The polymerase then catalyzes the incorporation of nucleoside monophosphates, beginning at the 3' end of the primer ("primer extension"), generally at 40° C. to 75° C.

The practical benefits of PCR nucleic acid amplification have been rapidly appreciated in the fields of genetics, molecular biology, cellular biology, clinical chemistry, forensic science, and analytical biochemistry. For example, see Erlich (ed.)*PCR Technology*, Stockton Press (New York) (1989); Erlich et al. (eds.), *Polymerase Chain Reaction*, Cold Spring Harbor Press (Cold Spring Harbor, N.Y.) (1989); Innis et al., *PCR Protocols*, Academic Press (New York) (1990); and White et al., *Trends in Genetics* 5/6: 185–189 (1989). PCR can replace a large fraction of molecular cloning and mutagenesis operations commonly performed in bacteria, having advantages of speed, simplicity, and lower cost. Furthermore, PCR permits the rapid and highly sensitive qualitative and even quantitative analysis of nucleic acid sequences.

Although one can move PCR reaction tubes manually back and forth between thermostated baths in each temperature range, PCR most commonly is performed in an automated temperature-controlled machine, known as a "thermal cycler," in which a microprocessor is programmed to change the temperature of a heat-exchange block or bath containing reaction tubes back and forth among several specified temperatures for a specified number of cycles, holding at each temperature for a specified time, usually on the order of one-half to two minutes. The total cycle time is usually less than 10 minutes, and the total number of cycles is usually less than 40, so that a single, multi-cycle amplification, amplifying the targeted nucleic acid sequence $10^5$ to $10^{10}$ times, normally occurs in less than seven hours and often less than four hours.

PCR has also been applied to amplify specific DNA segments inside cells, without first extracting the DNA from the cells. This technique is called in situ PCR. The cells may be individual cells, or part of a tissue sample. Most often, in situ PCR is performed on cells or thin slices of tissue ("tissue sections") mounted on microscope slides. Cells which do not form tissues, such as leukocytes and many cultured cells (such as HeLa cells), are spread out upon a slide by centrifugation, producing a "cytospin" preparation. The cells or tissue usually have been fixed by treatment with formalin, or other reagents ("fixatives"), so that their morphology is preserved and recognizable after PCR and subsequent detection of the amplified nucleic acid.

To perform in situ PCR on fixed cells or tissue samples on a glass microscope slide, the slide is pretreated with an agent that inhibits or prevents the cells or tissue from being removed during the PCR process, or during the subsequent treatments for visualization of the amplified nucleic acid. For example, the surface of the slide is treated so as to covalently bond 3-aminopropyl triethoxysilane, or the surface is coated with poly(lysine) or gelatin/chrome alum. The area of the slide with the specimen is then covered with PCR reagents. The slide and reagents are then cycled 10 to 40 times between temperatures typically between about 95° C. and 68° C., but sometimes as low as 37° C., spending at least a fraction of a minute or more at each of two or three selected temperatures during each cycle.

There are several important requirements that must be met during thermal cycling for in situ PCR to be successful. One is that evaporation of water from the PCR reagents must be prevented. No more than about 5% change from optimum PCR reagent concentrations can be tolerated without resulting in lower amplification yields or less specificity. Moreover, material which inhibits the PCR should be omitted from the process. In addition, bubbles of air or dissolved gas which are released by the reagents when they are heated should not disturb the access of the liquid reagent to the entire area to be processed. Furthermore, the conditions employed during the thermal cycling or subsequent processing to visualize the amplified nucleic acid should not disrupt tissue or cell morphology and should result in uniform and reproducible results.

Thus, in situ PCR requires a delicate balance between two opposite requirements of PCR in a cellular preparation: the cell and subcellular (e.g., nuclear) membranes must be permeabilized sufficiently to allow externally applied PCR reagents to reach the target nucleic acid, yet must remain sufficiently intact and nonporous to retard diffusion of amplified nucleic acid out of the cells or subcellular compartments where it is synthesized. In addition, the amplified nucleic acid must be sufficiently concentrated within its compartment to give a microscopically visible signal, yet remain sufficiently dilute that it does not reanneal between the denaturation and probe-annealing steps.

Nuovo et al. (U.S. Pat. No. 5,538,871) disclose that a commercially available thermal cycler, designed to accommodate multiple small plastic microcentrifuge tubes, can be modified to accommodate microscope slides. For example, it is disclosed that a single flat metal sample block can be machined to replace the top surface of a thermal cycler. It is also disclosed that the sample block can contain vertical slots in which the microscope slides are placed. However, Nuovo et al. do not disclose a device other than one having a metal sample block to perform PCR on microscope slides. Moreover, Nuovo et al. do not disclose a means to detect the temperature of the microscope slide during thermal cycling.

Lippman (U.S. Pat. No. 4,694,846) relates to a microscope slide system in which the slide is adapted for illuminating a sample in a depression on the upper surface of the slide. The sample has opaque particles suspended in a liquid, e.g., coal slurries. The Lippman patent discloses that the slide is heated by electrical resistive elements formed on the surface of the slide and a thermocouple may be attached to the slide so as to measure and control heat. The resistive elements and the thermocouple are each connected to an electrical source by wires. However, the Lippman patent does not mention a slide useful in a thermal cycling device, e.g., to amplify nucleic acids in a biological sample on the slide.

Thus, what is needed is an improved thermal cycling device for microscope slides.

SUMMARY OF THE INVENTION

The invention provides a thermal cycling device for regulating the temperature of a biological sample on a flat substrate, e.g., an optically transparent substrate which includes a glass substrate such as a microscope slide or a cover slip, or an optically transparent substrate which is electrically conductive, for example, glass which is doped so as to yield an electrically-conductive flat substrate, e.g., by depositing electrically resistive materials on the glass, or an optically transparent substrate that is doped so as to yield a substrate which absorbs a specific wavelength of light or other forms of radiation (e.g., acoustic or radio frequencies).

The invention also provides an apparatus comprising the flat substrate for use in the thermal cycling device of the invention. The apparatus comprises a flat substrate having at least a first pad and a second pad coupled therewith, and at least one heating element associated with the substrate. The flat substrate is defined in part by a first edge and a second edge, where the first pad is disposed along the first edge of the substrate and the second pad is disposed along the second edge of the substrate. Preferably, the first edge is opposite the second edge. The substrate is also defined, in part, by an upper and a lower surface. The first pad and the second pad, and the heating element(s), are preferably disposed on the lower surface of the substrate. The heating element(s) promote heat transfer from the substrate or a portion thereof to a sample disposed on the surface of the substrate. The heating element is preferably a light transparent thin-film heater which is preferably associated with, or coupled, deposited, affixed or attached to, the lower surface of the flat substrate. The heating element is coupled, thermally or electrically, between the first pad and the second pad. In one embodiment the invention, the resistance of a thin-film heating element associated with the substrate may be determined and employed to detect the temperature of the surface of the substrate. The substrate is further defined, in part, by a third edge and a fourth edge. A third pad and a fourth pad may be disposed along the third edge and the fourth edge, respectively, of the substrate. Preferably, the third edge is opposite the fourth edge. Also preferably, the third pad and the fourth pad are disposed on the upper surface of the substrate.

Thus, a preferred embodiment of the invention comprises an apparatus comprising a flat substrate having at least a first pad, a second pad, a third pad, and a fourth pad coupled thereto, at least one heating element associated with the substrate and coupled between the first and second pad, and at least one temperature-monitoring or temperature-sensing element or device associated with, e.g., attached or affixed to or deposited on, the substrate, and coupled between the third pad and the fourth pad. The temperature-monitoring element(s) detect the temperature of the flat substrate. Preferably, the temperature-monitoring element is associated with the upper surface of the flat substrate. Also, preferably, the temperature-monitoring element is a thin-film resistive temperature-monitoring element such as a thin-film platinum resistive temperature-monitoring element, a nickel-based temperature-monitoring element, a thermocouple, a thermodiode, a thermotransistor, thermoresistor or thermistor. A preferred temperature-monitoring element is a thin-film platinum resistive temperature-monitoring element. For example, the heating element(s) and temperature-monitoring element(s) may be parts of separate electrical circuits. Alternatively, each slide may contain a microfabricated array of heaters and temperature sensors terminating in leads. Thus in this embodiment, the heating element and temperature-monitoring element are integrated in a single electrical circuit, and an array comprises a multiplicity of these circuits, where each member of the array is independently controlled. If the heating element(s) and the temperature-monitoring element(s) are in such an array, they may be employed to create an isothermal surface or any desired temperature profile along the surface of the substrate. Thus, a device of the invention provides a method to vary the heating rate along the surface of the substrate, in addition to the temperature over time.

One embodiment of an apparatus of the invention is a self-heating microscope slide which comprises a slide, at least one heating element, and at least one temperature-sensing or -monitoring element.

Also provided is a method of using the apparatus of the invention, for example, to thermal cycle a sample present on the slide, in a thermal cycling device. The thermal cycling device of the invention preferably comprises a housing, a control system for regulating temperature, e.g., a computerized control system, conductive clips, and a cooling device, e.g., a thermoelectric refrigeration unit or fan. Optionally, the device further comprises a support or sample plate or holder, e.g., as part of the upper wall of the housing, for at least one apparatus of the invention. The apparatus preferably comprises a microscope slide having at least one biological sample, such as a tissue section, on the upper surface of the slide. The sample is overlaid with a volume of liquid, e.g., reagents for in situ PCR, and then the liquid is overlaid with a water impermeable barrier, e.g., a cover slip. The heating element of the apparatus is operatively connected to the control system by contacting the first and second pads of the apparatus to a first and second connector, e.g., a conductive clip, respectively. The connector may, for example, be a spring loaded or mechanically actuated edge-connector or an alligator clip, and may be fixed or removable or any combination thereof. The temperature-monitoring device of the apparatus is operatively connected to the control system by contacting the third and fourth pads of the apparatus with a third and fourth conductive clip, respectively. Alternatively, the apparatus is placed on a support or sample plate, for example, one having at least one opening or gap dimensioned to correspond to the dimensions of the apparatus. Then the apparatus is operatively connected to the first, second, third, and fourth connectors.

In order to rapidly cool the substrate, the device of the invention includes a cooling device. The cooling device forces cool, e.g., ambient, air toward the apparatus and/or sample plate and disperses air located between the cooling device and the sample plate. Preferably, the cooling device is an appropriately positioned fan, e.g., one placed beneath and parallel to, or at an angle to, e.g., 90°, the apparatus or sample plate. Preferably, the fan is controlled by a relay switch. Once a heating cycle is completed, the fan sweeps ambient temperature air across the lower surface of the apparatus, and sweeps hot air out of the device. Alternatively, the fan may be employed in exhaust mode to disperse air away from the apparatus and/or sample plate. Optionally, a refrigerated cooling device may be employed for achieving lower than ambient temperatures. For example, a refrigerator coil may be positioned beneath the apparatus or sample plate, and positioned above the fan. Alternatively, a refrigerator cooling plate or thermoelectrically cooled fins which are positioned beneath the apparatus and/or sample plate may be employed. Thus, the present invention allows heating and cooling of a sample to take place both quickly and uniformly. The device may be constructed so as to thermal cycle samples on one or more flat substrates.

A computerized control system maintains temperature uniformity across the surface of each apparatus during heating or cooling. It is preferred that the substrates are heated electrically and cooled by convection, e.g., for in situ polymerase chain reaction (PCR) to detect and/or diagnose a disease, such as diagnosing AIDS and other human diseases. The present device outperforms currently available thermal cycling devices because it does not employ an external heat sink to facilitate heat transfer. Moreover, the present invention directly measures and regulates the temperature of the sample which is subjected to thermal cycling, in contrast to currently available devices which measure the temperature of the metal sample block or other heat transfer medium, and so provides greater temperature uniformity. Furthermore, the device of the invention is simpler in design and thus less costly to manufacture than currently available thermal cyclers. In particular, the device of the invention is simpler in design than the device disclosed in copending U.S. application Ser. No. 08/810,641, which employs a ceramic sample plate to transfer heat to a microscope slide. The device preferably comprises a housing or body, which comprises a lower hollow enclosure or compartment and optionally an upper hollow enclosure or compartment, i.e., a lid or cover. If present, the support or sample plate may rest on the uppermost edges of the sidewalls and endwalls of the housing to form the lower enclosure. Alternatively, the support or sample plate may rest on protrusions from the inner side and/or end walls, or be attached or affixed to the inner sidewalls and/or endwalls, to form the lower hollow enclosure. In another embodiment, the first, second, third and fourth conductive clips are associated with the sidewalls and/or endwalls of the housing. The housing and the support or sample plate preferably comprise polystyrene, polypropylene, polyethylene, or other plastics with compatible electrical and thermal conductances.

The device of the invention also may comprise a controller or computer. The controller or computer, e.g., a commercial microcomputer or a self-contained microprocessor, executes commands written in software so as to turn on and off the heating and cooling elements so that the biological sample on the flat surface is subjected to a predetermined temperature versus time profile. For example, a microprocessor may be associated with the sample plate or apparatus, or in a location other than the sample plate or apparatus. These heating and cooling cycles correspond to the denaturation, annealing and elongation steps in a PCR.

Therefore, the device of the invention is useful for temperature-sensitive manipulations of nucleic acids or proteins, or cell preparations or living cells, that are performed on microscope slides and other substantially flat substrates employed in medical diagnostics, molecular biology, and cellular biology, at temperatures that range from ambient to 100° C. In particular, the device is useful for in situ PCR of a biological sample present on the flat substrate, e.g., in a method to detect the presence of the nucleic acid or protein of a pathogen, such as a virus, bacterium or fungus, in a method to detect the presence of nucleic acid sequences associated with a genetic disease, nucleic acid hybridizations, e.g., Northern and Southern blot hybridizations, or in situ hybridization of nucleic acids. For a review of in situ hybridization, see Nagai et al., 1987, *Intl. J Gyn. Path.* 6:366–379.

PCR amplified nucleic acid, or RNA or DNA that is present in a cell in an amount that is detectable without amplification, can then be detected, for example, with a radiolabeled probe. Moreover, if the biological sample comprises protein, e.g., a tissue section, the sample can also be mixed with a moiety, e.g., antibodies, which specifically bind to a cellular protein to form a complex, and the complex subsequently detected ("immunocytochemistry"). The combination of in situ PCR and immunocytochemistry can identify the presence of a specific nucleic acid sequence and a specific protein in a single cell in a biological sample. The device of the invention is also useful to perform a ligase chain reaction (LCR), a cyclic two-step reaction. The first step in LCR is a denaturation step. The second step is a cooling step in which two sets of adjacent, complementary primers anneal to a single-stranded target DNA molecule and are ligated together by a DNA ligase enzyme. The product of ligation from one cycle serves as a template for the ligation reaction of the next cycle. LCR results in the exponential amplification of ligation products.

In one embodiment of the invention, a device is provided for subjecting at least one biological sample disposed on at least one flat substrate to thermal cycling. The device preferably comprises: a means for holding or supporting at least one apparatus comprising a flat substrate, a temperature-monitoring element and a heating element; a means for cooling the lower surface of the apparatus; and a means for controlling, wherein the controlling means is operatively connected to the temperature-monitoring element, to the heating element and to the means for cooling, such that the temperature of the substrates can be rapidly and controllably increased and decreased by the control means in response to the temperature sensed by the temperature-monitoring element such that the biological sample can be subjected to rapid thermal cycling over a temperature range of at least 40° C., preferably at least 30° C. The cooling means may comprise a pulsating membrane, or flow out of an air conditioning duct, compressed air tank or supply line. Preferably, the cooling means comprises a rotating means for dispersing air. The means for holding or supporting may include clips, e.g., attached to a support plate which comprises a gap or opening dimensioned for an apparatus of the invention. Thus, the device of the invention is useful for the amplification of nucleic acids, e.g., in a biological sample. The device is also useful for maintaining the temperature of at least one biological sample which is disposed on at least one substantially flat substrate, and for the in situ hybridization of nucleic acids.

The invention also provides a method for thermal cycling, or maintaining the temperature of, a biological sample on a substantially flat surface. One embodiment of the invention comprises a method for amplifying target nucleic acid. The method comprises contacting a biological sample which comprises nucleic acid, and which is disposed on an apparatus of the invention, with an amount of PCR reagents so as to yield a mixture. The mixture is subjected to thermal cycling by placing the apparatus in a device of the invention so as to yield amplified nucleic acid.

Also provided is a method for in situ PCR amplification of a biological sample comprising a target nucleic acid. The method comprises contacting an apparatus of the invention comprising the sample, e.g., a sample comprising fixed cells suspected of containing the target nucleic acid, and an amount of PCR reagents sufficient to amplify the target nucleic acid so as to form a mixture on the surface of the apparatus. The mixture is then subjected to thermal cycling by placing the apparatus having the mixture in the device of the invention so as to yield amplified nucleic acid.

Further provided is a method for in situ hybridization of a target nucleic acid in a sample. The method comprises contacting an apparatus of the invention comprising the sample, e.g., a sample comprising the target nucleic acid, with an amount of a labeled probe comprising a preselected DNA comprising the target nucleic acid sequence to as to form a mixture comprising the sample and the probe. The temperature of the mixture is maintained for a sufficient time to form binary complexes between at least a portion of the probe and the target nucleic acid by placing the apparatus having the mixture in a device of the invention. Then the absence or presence of the binary complexes is detected.

Yet another embodiment of the invention is a method for in situ hybridization of target nucleic acid wherein the target nucleic acid is spatially confined to individual cells containing the target nucleic acid. The method comprises contacting an apparatus of the invention comprising the sample, e.g., a sample comprising fixed cells suspected of containing the target nucleic acid, with an amount of a labeled probe comprising a preselected DNA comprising the target nucleic acid sequence so as to form an apparatus comprising mixture. The temperature of the mixture is maintained for a sufficient time to form binary complexes between at least a portion of the probe and the target nucleic acid by placing the apparatus with the mixture in a device of the invention. The absence or presence of binary complexes is then detected.

Yet another embodiment of the invention is a method for hybridization of isolated nucleic acid to target nucleic acid disposed on a flat substrate, e.g., formed of glass or silicon. The method comprises contacting the isolated nucleic molecule, e.g., labeled nucleic acid, with a flat substrate comprising at least one sample comprising the target nucleic acid under conditions sufficient to form binary complexes between at least a portion of the isolated nucleic acid and the target nucleic acid. Then the presence or absence of complexes is determined or detected.

The invention also provides a thermal cycling device for regulating the temperature of a flat substrate, e.g., a microscope slide or a cover slip. The thermal cycling device of this embodiment of the invention comprises a flat silicon sample plate or block for holding at least two flat substrates. One substrate, the control, is attached to a means for sensing the temperature of the substrate. The other substrate(s) ("test" samples) comprises a biological sample, such as a tissue section, on the upper surface of the substrate. The test samples are overlaid with a volume of liquid, e.g., reagents for in situ PCR, and then the liquid is overlaid with a water impermeable barrier, e.g., a cover slip. The substrates are then thermal cycled.

The present invention outperforms currently available thermal cycling devices because it transfers heat through a silicon sample plate that is thinner than the metal, i.e., aluminum, sample plate required for thermoelectric units of the Peltier type. Thus, the invention provides a device in which a silicon sample plate transfers heat more rapidly to a flat substrate, which comprises a biological sample, than currently available thermal cycling devices. Moreover, the device of the invention measures the temperature of the substrate directly, in contrast to currently available devices which measure the temperature of the metal sample block or other heat transfer medium, or measure the temperature of the liquid on the surface of a microscope slide. Furthermore, the device of the invention is simpler in design and thus less costly to manufacture than currently available thermal cyclers.

The device is preferably contained in a housing or body, which comprises a lower hollow enclosure or compartment and an upper hollow enclosure or compartment, i.e., a lid or cover. The housing preferably comprises polystyrene, polypropylene, polyethylene, or other plastics with compatible electrical and thermal conductances. The silicon sample plate rests on the uppermost edges of the sidewalls and endwalls of, or is mounted to the inner sidewalls and/or endwalls of, the lower hollow enclosure.

In one embodiment of the invention, the sample plate comprises a silicon sample plate which has a horizontal flat upper surface dimensioned to hold at least two microscope slides with their largest dimensions oriented horizontally. For example, a silicon sample plate with dimensions of about 6.5 inches in length, and about 3.5 inches in width can accommodate six microscope slides, although other dimensions are within the scope of the invention.

Alternatively, the silicon sample plate may have at least two recesses, or wells, suitable for holding individual flat substrates, e.g., a rectilinear recess for a microscope slide, a water impermeant barrier and a volume of a vapor barrier, e.g., mineral oil, which prevents drying of the liquid film which covers the biological sample during thermal cycling.

The invention also provides a silicon sample plate which comprises one or more substantially vertically oriented slots, which substantially and closely enclose the flat substrate, e.g., a rectilinear slot for a microscope slide with its largest dimensions oriented in an approximately vertical plane. Such orientation substantially increases the number of substrates comprising biological samples which can be analyzed at one time.

The device of the invention also comprises a temperature sensor that detects the temperature of a flat substrate. Preferably, the sensor is attached or affixed to the upper surface of a control flat substrate.

The device of the invention also comprises a computer-regulated conductive heating means so as to regulate the heat transfer from the silicon sample plate to a flat substrate disposed on the sample plate. The means of heating is preferably an etched foil heater, a kapton-insulated-etched foil heater, a wire wound resistive heater or a silicone rubber insulated wire wound resistive heater, affixed or attached, e.g., glued, to the lower surface of the silicon sample plate. Preferably, the heater is electrically insulated and controlled by a relay switch.

In order to rapidly cool the sample plate, the device of the invention includes a means for cooling the sample plate. The means for cooling the sample plate comprises a means for forcing cool, i.e., ambient, air toward the means for heating the sample plate and a means for dispersing air located between the means for cooling and the means for heating. Preferably, the means for forcing cool air toward the sample plate and the means for dispersing the air are the same, i.e., an appropriately positioned fan. Preferably, the cooling means is a fan placed beneath and parallel to, or at an angle to, e.g., 90°, the heating means. Preferably, the fan is controlled by a relay switch. Optionally, a refrigerated means of cooling may be employed for lower than ambient temperatures. Thus, once a heating cycle is completed, the fan sweeps ambient temperature air across the lower surface of the heater, and sweeps hot air out of the device. Thus, the present invention allows heating and cooling of a sample to take place both quickly and uniformly.

The device of the invention also comprises a controller or computer. The controller or computer, e.g., a commercial microcomputer or a self-contained microprocessor, executes commands written in software so as to turn on and off the heating and cooling elements so that the biological sample on the flat surface is subjected to a predetermined temperature versus time profile. These heating and cooling cycles correspond to the denaturation, annealing and elongation steps in a PCR.

Therefore, the device of the invention is useful for temperature-sensitive manipulations of nucleic acids or proteins, or cell preparations or living cells, that are performed on microscope slides and other flat substrates employed in medical diagnostics, molecular biology, and cellular biology, at temperatures that ranges from ambient to 100° C., e.g., the device is useful for in situ PCR of a biological sample present on the flat substrate.

In one embodiment of the invention, a device is provided for subjecting a plurality of biological samples disposed on at least one flat substrate to thermal cycling. The device preferably comprises: a thermal sensing means placed on the upper surface of one flat substrate and at least one flat substrate lacking the thermal sensing means and comprising at least one biological sample; a means for holding the plurality of flat substrates, wherein the means for holding comprises a silicon sample plate, and wherein the flat substrates are disposed on the upper surface of the holding means; means for heating the lower surface of the means for holding, the means for heating is positioned parallel to and in close proximity to the means for holding; means for cooling the lower surface of the means for heating, wherein the means for cooling comprises a rotating means for dispersing air beneath the means for heating; and a means for controlling, wherein the controlling means is operatively connected to the means for thermal sensing, the means for heating and the means for cooling such that the temperature of the substrates can be rapidly and controllably increased and decreased by the control means in response to the temperature sensed by the means for sensing such that the biological sample can be subjected to rapid thermal cycling over a temperature range of at least 40° C.

Another preferred embodiment of the invention is a thermal cycling device useful for the amplification of nucleic acids. The device preferably comprises: a thermal sensing means placed on the upper surface of one flat substrate and at least one flat substrate lacking the thermal sensing means and comprising at least one biological sample; a means for holding the plurality of flat substrates, wherein the means for holding comprises a silicon sample plate, and wherein the flat substrates are disposed on the upper surface of the holding means; a means for heating the lower surface of the means for holding, wherein the means for heating is attached to the means for holding; a means for cooling the lower surface of the means for heating, wherein the means for cooling comprises a rotating means for dispersing air beneath the means for heating; and a means for controlling, wherein the controlling means is operatively connected to the means for thermal sensing, the means for heating and the means for cooling such that the temperature of the substrates can be rapidly and controllably increased and decreased by the control means in response to the temperature sensed by the means for sensing such that the biological sample can be subjected to rapid thermal cycling over a temperature range of at least 30° C.

Further provided is a device for maintaining the temperature of a plurality of biological samples which are disposed on at least one flat substrate. The device comprises: a thermal sensing means placed on the surface of one flat substrate and at least one flat substrate lacking the thermal sensing means and comprising at least one biological sample; a means for holding the plurality of flat substrates, wherein the means for holding comprises a silicon sample plate, and wherein the flat substrates are disposed on the surface of the holding means; a means for heating the surface of the means for holding, wherein the means for heating is positioned in close proximity to the means for holding; a means for cooling the surface of the means for heating, wherein the means for cooling comprises a rotating means for dispersing air; and a means for controlling, wherein the controlling means is operatively connected to the means for thermal sensing, the means for heating and the means for cooling such that the temperature of the substrates can be maintained at a particular temperature by the control means in response to the temperature sensed by the means for sensing such that the biological sample can be maintained at a particular temperature over a temperature range of at least 40° C.

Also provided is a device useful for the in situ hybridization of nucleic acids. The device comprises: a thermal sensing means placed on the surface of one flat substrate and at least one flat substrate lacking the thermal sensing means and comprising at least one biological sample; a means for holding the plurality of flat substrates, wherein the means for holding comprises a silicon sample plate, and wherein the flat substrates are disposed on the surface of the holding means; a means for heating the lower surface of the means for holding, wherein the means for heating is attached to the means for holding; a means for cooling the lower surface of the means for heating, wherein the means for cooling comprises a rotating means for dispersing air; and a means for controlling, wherein the controlling means is operatively connected to the means for thermal sensing, the means for heating and the means for cooling such that the temperature of the substrates can be maintained at a particular temperature by the control means in response to the temperature sensed by the means for sensing such that the biological sample can be maintained at a particular temperature over a temperature range of at least 30° C.

The invention also provides a device for subjecting a biological sample to thermal cycling. The device comprises: a housing; a flat substrate having a thermal sensor coupled to the flat substrate, the flat substrate having a biological samples disposed thereon; a holder for the flat substrate, the holder attached to the housing, wherein the holder comprises a silicon sample plate, and wherein the flat substrate is disposed on the upper surface of the silicon sample plate; a cooler for the flat substrate, the cooler attached to the housing; and a heater thermally coupled to the flat substrate.

Also provided is a device for maintaining the temperature of a biological sample. The device comprises:a housing; a flat substrate having a thermal sensor coupled to the flat substrate, the flat substrate having a biological samples disposed thereon; a holder for the flat substrate, the holder attached to the housing, wherein the holder comprises a silicon sample plate, and wherein the flat substrate is disposed on the upper surface of the silicon sample plate; a cooler for the flat substrate, the cooler attached to the housing; and a heater thermally coupled to the flat substrate.

The invention also provides a method for thermal cycling, or maintaining the temperature of, a biological sample on a flat surface. One embodiment of the invention comprises a method for amplifying target nucleic acid. The method comprises:

(a) contacting a biological sample, which comprises nucleic acid, that is disposed on a flat substrate with an amount of PCR reagents so as to yield a mixture;

(b) subjecting the mixture to thermal cycling in the device of the present invention so as to yield amplified nucleic acid.

Also provided is a method for in situ PCR amplification of target nucleic acid wherein the amplified nucleic acid is spatially confined to individual cells originally containing the target nucleic acid. The method comprises (a) contacting fixed cells suspected of containing the target nucleic acid with an amount of PCR reagents sufficient to amplify the target nucleic acid so as to form a mixture; and (b) subjecting the mixture to thermal cycling in the device of the present invention so as to yield amplified nucleic acid.

Further provided is a method for in situ hybridization of a target nucleic acid wherein the target nucleic acid is spatially confined to a flat surface. The method comprises:

(a) contacting the target nucleic acid with an amount of a labeled probe comprising a preselected DNA comprising the target nucleic acid sequence to as to form a mixture;

(b) maintaining the temperature of the mixture for a sufficient time to form binary complexes between at least a portion of the probe and the target nucleic acid, wherein the temperature is maintained on the device of the present invention; and (c) detecting the absence or presence of the binary complexes.

Yet another embodiment of the invention is a method for in situ hybridization of target nucleic acid wherein the target nucleic acid is spatially confined to individual cells originally containing the target nucleic acid. The method comprises:

(a) contacting fixed cells suspected of containing the target nucleic acid with an amount of a labeled probe comprising a preselected DNA comprising the target nucleic acid sequence so as to form a mixture; and (b) maintaining the temperature of the mixture for a sufficient time to form binary complexes between at least a portion of the probe and the target nucleic acid, wherein the temperature is maintained on the device of the invention; and (c) detecting the absence or presence of the binary complexes.

DETAILED DESCRIPTION OF THE INVENTIONS

Definitions

Figure 1:
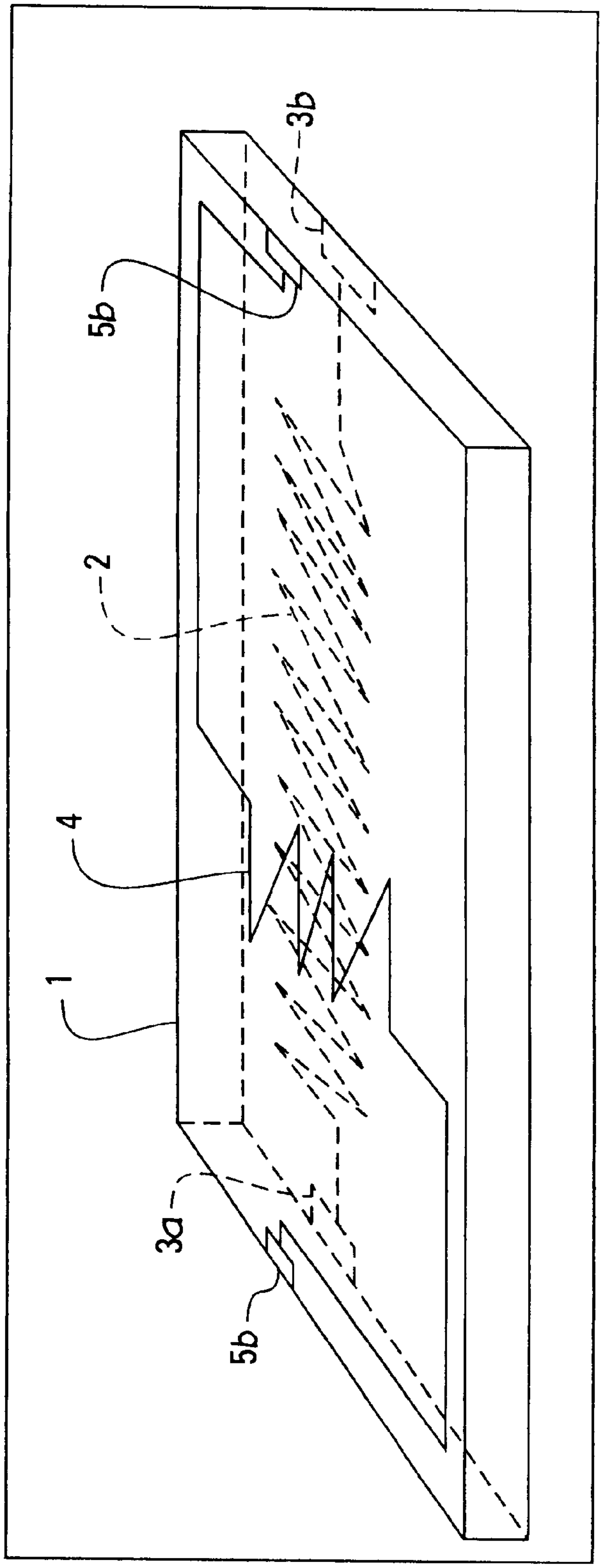
FIG. 1 illustrates a side view of a preferred embodiment of an apparatus of the invention.

As used herein, a "substantially flat substrate" means a material on which isolated nucleic acid, polypeptide or protein, or intact cells or tissues, can be maintained for an indefinite period of time. The substrate is preferably optically transparent. Thus, materials such as glass, doped glass and the like are substantially flat substrates within the scope of the invention. As used herein, the term "biological sample" includes isolated and/or purified nucleic acid or polypeptide, or intact cells present in a specimen or sample obtained from any prokaryotic or eukaryotic organism, e.g., blood or a biopsy sample from a mammal, for example, a human or non-human mammal, e.g., a bovine, ovine, swine, caprine, equine, canine or feline. More than one biological sample may be present on any one flat substrate. A preferred biological sample is a mammalian tissue section. As used herein, the terms "isolated and/or purified" refer to in vitro isolation of a nucleic acid or polypeptide molecule from its natural cellular environment, and from association with other components of the cell, such as nucleic acid or protein.

"PCR" refers to a process of amplifying one or more specific nucleic acid sequences, wherein 1) oligonucleotide primers which determine the ends of the sequences to be amplified are annealed to single-stranded nucleic acid in a test sample, 2) a nucleic acid polymerase extends the 3' ends of the annealed primers to create a nucleic acid strand complementary in sequence to the nucleic acid to which the primers were annealed, 3) the resulting double-stranded nucleic acid is denatured to yield two single-stranded nucleic acids, and 4) the processes of primer annealing, primer extension, and product denaturation are repeated enough times to generate easily identified and measured amounts of the sequences defined by the primers. Practical control of the sequential annealing, extension, and denaturation steps is exerted by varying the temperature of the reaction container, normally in a repeating cyclical manner. Annealing and extension occur optimally in about the 35° C. to 80° C., preferably about the 40° C. to 75° C. temperature range, whereas denaturation requires temperatures in about the 80° C. to 100° C. range.

While a single primer pair is most often employed in PCR, a single primer ("one-sided PCR"), multiple primers ("multiplex PCR"), degenerate primers, and nested primers may also be employed in the methods of the invention. Moreover, in addition to amplification of DNA, the device and method of the invention can be employed for RT-PCR, i.e., reverse transcription of an RNA molecule to produce a single stranded cDNA with subsequent PCR of the cDNA.

PCR specificity may be increased by omitting at least one reagent necessary for PCR until the sample temperature is between 50–80° C. ("Hot Start™"), the addition of a reagent which interferes with nonspecific polymerase reactions (e.g., SSB), or the addition of a modified nucleotide (e.g., dUTP) and the corresponding glycosylase (e.g., UNG) into the reaction mixture. See U.S. Pat. No. 5,538,871, the disclosure of which is incorporated by reference herein.

"Thermal cycling" commonly is automated by a "thermal cycler," an instrument which, for example, rapidly (e.g., on the time scale of one to several minutes) heats and cools a sample compartment, a partially or completely enclosed container holding the vessel, e.g., a microcentrifuge tube, or a flat substrate, e.g., a microscope slide, on which nucleic acid amplification occurs and the heat-transfer medium directly contacting the PCR vessel or flat substrate. Most commonly, the sample compartment is a "sample block," which can be temperature controlled. Conventional sample blocks are manufactured from metal and contain wells designed to fit tightly the plastic microcentrifuge tubes in which PCR amplification normally is performed.

"PCR reagents" refers to the chemicals, apart from the biological sample, needed to make nucleic acid amplification work. The reagents consist of five classes of components: (1) an aqueous buffer, (2) a water-soluble magnesium salt, (3) at least four deoxyribonucleotide triphosphates (dNTPs), although these can be augmented or sometimes replaced by dNTPs containing base analogues which Watson-Crick base-pair like the conventional four bases, such as the analog deoxyuridine triphosphate (dUTP) and dUTP carrying molecular tags such as biotin and digoxigenin, covalently attached to the uracil base via spacer arms, (4) oligonucleotide primers (normally two for each target sequence, with sequences which define the 5' ends of the two complementary strands of the double-stranded target sequence), and (5) a polynucleotide polymerase, preferably a DNA polymerase, most preferably a thermostable DNA polymerase, which can tolerate temperatures between 90° C. and 100° C. for a total elapsed time of at least 10 minutes without losing more than about half of its activity.

"Fixed cells" refers to a sample of cells which has been chemically treated to strengthen cellular structures, particularly membranes, against disruption by solvent changes, temperature changes, mechanical stresses, and drying. Cells may be fixed either in suspension or while contained in a sample of tissue, such as might be obtained during autopsy, biopsy, or surgery. Cell fixatives generally are chemicals which crosslink the protein constituents of cellular structures, most commonly by reacting with protein amino groups. Preferred fixatives are buffered formalin, 95% ethanol, formaldehyde, paraformaldehyde, or glutaraldehyde. Fixed cells also may be treated with proteinases, enzymes which digest proteins, or with surfactants or organic solvents which dissolve membrane lipids, in order to increase the permeability of fixed cell membranes to PCR reagents. Such treatments must follow fixation to assure that membrane structures do not completely fall apart when the lipids are removed or the proteins are partially cleaved. Protease treatment is preferred following fixation for more than one hour and is less preferred following shorter fixation intervals. For example, a ten-minute fixation in buffered formalin, without protease treatment, is standard after suspended cells (e.g., from blood) have been deposited centrifugally on a slide by cytospin procedures standard in the cytochemical art.

A preferred mode of fixing cell samples for in situ PCR according to the present invention is to incubate them in 10% formalin, 0.1 M Na phosphate, pH 7.0, for a period of 10 minutes to 24 hours at room temperature. The cells may be a suspension, as would be obtained from blood or a blood fraction such as buffy coat, or may be a solid tissue, as would be obtained from biopsy, autopsy, or surgical procedures well known in the art of clinical pathology. If PCR is to be performed in cell suspension, suspended cells preferably are centrifuged after formalin fixation, resuspended in phosphate-buffered saline, and re-centrifuged to remove the fixative. The washed, pelleted cells may be resuspended in PCR buffer and added directly to a PCR tube. If PCR is to be performed on a microscope slide, suspended cells preferably are deposited on the slide by cytospin, fixed 10 minutes in buffered formalin, washed 1 minute in water, and washed 1 minute in 95% ethanol. Alternatively, suspended cells can be pelleted in a centrifuge tube and the pellet can be embedded in paraffin and treated like a tissue specimen. Tissue samples may be processed further and then embedded in paraffin and reduced to serial 4–5 μm sections by microtome procedures standard in the art of clinical pathology. Histochemical sections are placed directly on a microscope slide. In either case, the slide preferably will have been treated with 2% 3-aminopropyltriethoxysilane in acetone and air dried. After smears or sections have been applied to slides, the slides are heated at about 60° C. for about 1 hour. Paraffin-embedded sections can be deparaffinized by 2 serial 5 minute washes in xylene and 2 serial 5 minute washes in 100% ethanol, all washes occurring at room temperature with gentle agitation.

"Histochemical section" refers to a solid sample of biological tissue which has been frozen or chemically fixed and hardened by embedding in a wax or a plastic, sliced into a thin sheet, generally several microns thick, and attached to a microscope slide.

"Cytochemical smear" refers to a suspension of cells, such as blood cells, which has been chemically fixed and attached to a microscope slide.

"Vapor barrier" refers to an organic material, in which water is insoluble, which covers a PCR reaction or preparation in a way which substantially reduces water loss to the atmosphere during thermal cycling. Preferred vapor barrier materials are liquid hydrocarbons such as mineral oil, or paraffin oil, although some synthetic organic polymers, such as fluorocarbons and silicon rubber, also may serve as effective PCR vapor barriers. Waxes which are solid at temperatures below about 50° C. and liquid at higher temperatures also make convenient vapor barriers.

To isolate the PCR reagents from the atmosphere and from the vapor barrier, a thin, "water-impermeant barrier" such as a plastic or glass film, e.g., a glass cover slip or a polypropylene cover slip, is placed over the liquid film which comprises the PCR reagents. The water-impermeant barrier is generally attached to the microscope slide. For example, a cover slip can be placed over the liquid film and sealed to the microscope slide with nail polish or a similar adhesive. See Komminoth et al., *Diagnostic Molecular Pathology,* 1(2), 85–89 (1992). The cover slip can also be clipped to the slide. See U.S. Pat. No. 5,527,510. Alternatively, a gasket can be placed between the cover slip and a chambered slide, which contains the PCR reagent, sealed with 2.5% hot agarose and the assembly covered with saran wrap. See, Chiu et al., *Histochem. and Cytochem.,* 40, 333–341 (1992). However, any other fastening mechanism may be employed to attach the cover slip to a microscope slide, such as the use of other high temperature resistant adhesives.

"Detection" of PCR-amplified nucleic acid refers to the process of observing, locating, or quantitating an analytical signal which is inferred to be specifically associated with the product of PCR amplification, as distinguished from PCR reactants. The analytical signal can result from visible or ultraviolet absorbance or fluorescence, chemiluminescence, or the photographic or autoradiographic image of absorbance, fluorescence, chemiluminescence, or ionizing radiation. Detection of in situ PCR products involves microscopic observation or recording of such signals. The signal derives directly or indirectly from a molecular “tag” attached to a PCR primer or dNTP or to a nucleic acid probe, which tag may be a radioactive atom, a chromophobe, a fluorophore, a chemiluminescent reagent, an enzyme capable of generating a colored, fluorescent, or chemiluminescent product, or a binding moiety capable of reaction with another molecule or particle which directly carries or catalytically generates the analytical signal. Common binding moieties are biotin, which binds tightly to streptavidin or avidin, digoxigenin, which binds tightly to anti-digoxigenin antibodies, and fluorescein, which binds tightly to anti-fluorescein antibodies. The avidin, streptavidin, and antibodies are easily attached to chromophores, fluorophores, radioactive atoms, and enzymes capable of generating colored, fluorescent, or chemiluminescent signals.

“Nucleic acid probe” or “probe” refers to an oligonucleotide or polynucleotide containing a sequence complementary to part or all of the PCR target sequence, also containing a tag which can be used to locate cells in an in situ PCR preparation which retains the tag after mixing with nucleic acid probe under solvent and temperature conditions which promote probe annealing to specifically amplified nucleic acid.

Device of the Invention

Figure 2:
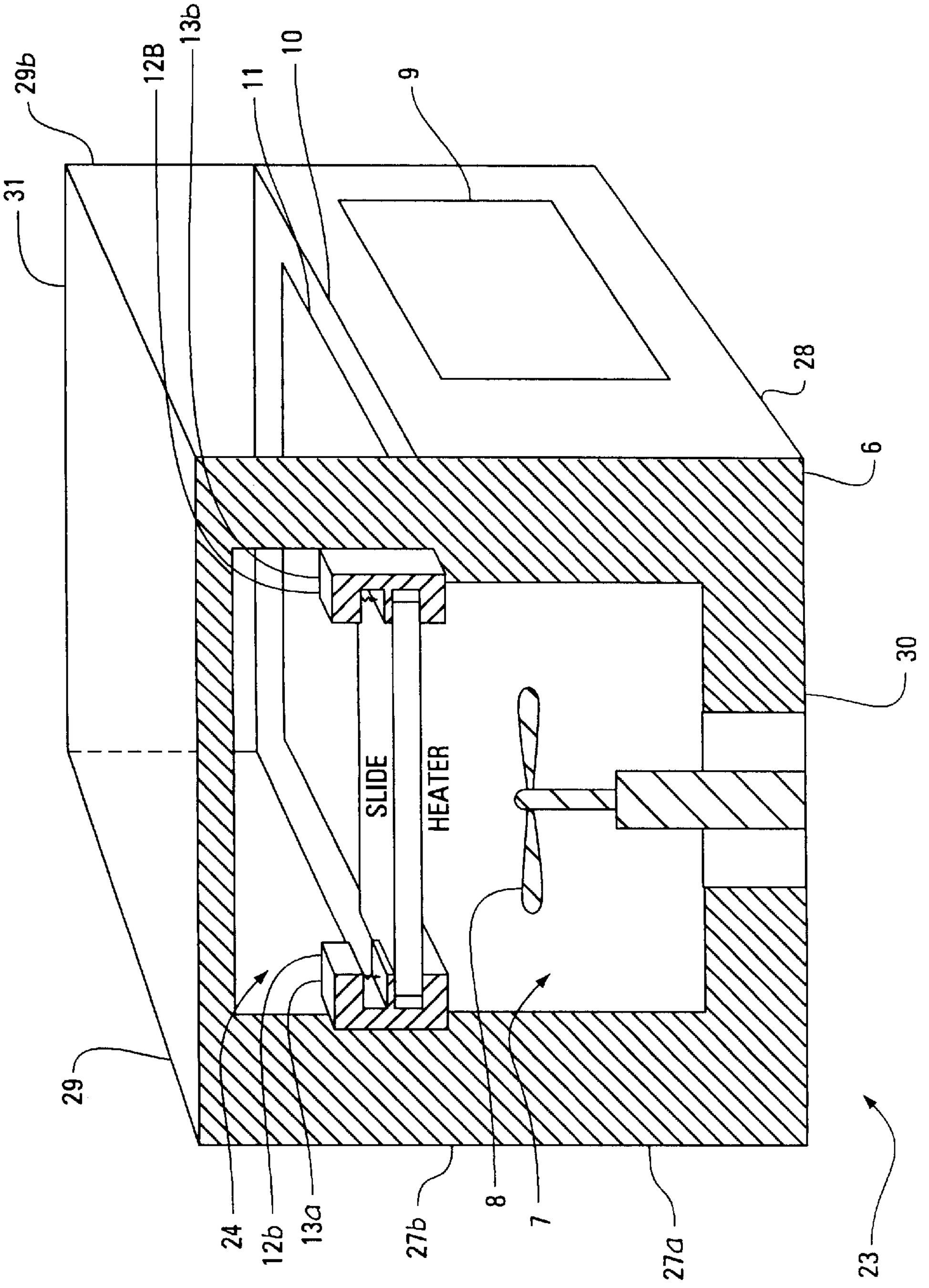
FIG. 2 illustrates a side view of a preferred embodiment of a device of the invention.

The invention provides a thermal cycler that optimizes heat flow to and from an apparatus preferably comprising at least one biological sample attached or affixed to a flat substrate, e.g., a microscope slide, present on the upper surface of the substrate. FIG. 1 shows a preferred embodiment of an apparatus of the invention. The apparatus comprises a microscope slide 1 with a microfabricated heater 2 and its associated conductive pads 3*a* and 3*b* on the lower surface, and with a resistive temperature sensor 4 and its associated conductive pads 5*a* and 5*b* on the upper surface, of the slide. The thermal cycler may comprise a sample or support plate useful for an apparatus of the invention. For in situ PCR applications, the surface of the sample or support plate may be designed to create openings proportioned for slides so that the large dimensions of the slide are horizontal and parallel to the plate. For example, FIG. 2 illustrates a side view of a preferred embodiment of a device of the invention. The housing 6 comprises a hollow compartment 7, with a propeller-type fan 8 mounted on the bottom of the housing, with its blades parallel to the lower surface or wall of the housing. One sidewall 27 or endwall 28 of the lower compartment has a 2 inch×2 inch outlet opening 9 for the fan's air intake. The upper surface of the support or sample holder 10 has an opening 11 for the microscope slide. Conductive clips 12*a* and 12*b*, for attachment to conductive pads on the apparatus, are on two parallel edges of the opening. Conductive clips 13*a* and 13*b*, for attachment to conductive pads on the apparatus, are on the two other parallel edges of the opening.

Figure 3:
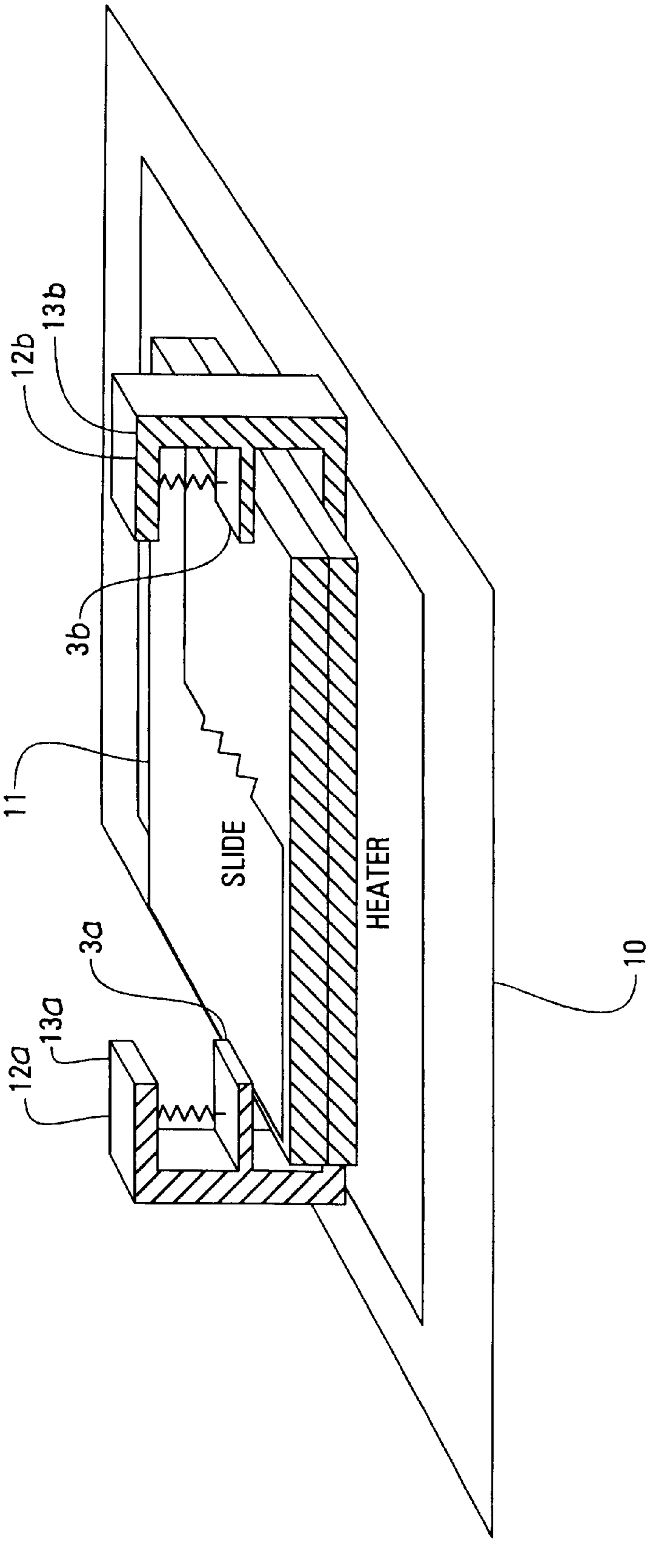
FIG. 3 illustrates an end-on view of a device of the invention.

FIG. 3 illustrates an end-on view of the microscope slide 1 with its heater-associated conductive pad 3*a* attached to a conductive clip 12*a*. The connection creates a vent 11 between the slide and the sample holder 10. When the fan is operative, air is drawn through the intake vent 9, swept across the slide, and forced through the exit vent 11. For microscope slides, the opening is about 16 mm wide and 77 mm long. Alternatively, conductive clips associated with the housing of a thermal cycler may be employed to hold an apparatus of the invention.

The device of the invention 23 is preferably enclosed in a housing or body 6 which comprises a lower hollow compartment 7 and optionally an upper hollow compartment 24, which may be formed by a lid 29. Although the two compartments 24 and 7 may be formed in any suitable, compatible and practical shape, together they are preferably box-shaped. Each compartment comprises a pair of sidewalls 27*a* and 27*b* and a pair of endwalls 28*a* and 28*b*. The lid 29 comprises a substantially flat upper surface 31 attached to or associated with the sidewalls and endwalls of the lid. The lower compartment 7 comprises a substantially flat lower surface 30 the outer surface on which, preferably, are feet. The side walls 27 or end walls 28 of the lower compartment 7 may comprise an inlet opening 9 for ambient air intake. The lower surface 30 of the lower compartment is attached to the sidewalls 27*a* and 27*b* and endwalls 28*a* and 28*b* of the lower compartment 7.

The housing 6 may be fabricated from any available material, e.g., a plastic, metal, such as stainless steel, ceramic, glass or combinations of any of the foregoing materials. However, it is preferred that the material be plastic, such as polypropylene or polycarbonate or the like, so that the housing may be molded in an inexpensive fashion. Moreover, it is preferred that the walls of the housing, including sidewalls 27*a* and 27*b*, endwalls 28*a* and 28*b*, lower surface 30, and upper surface 31, be relatively thin in dimension in order to provide a housing with low thermal mass. The most straightforward, but not necessarily limitative, construction of housing is one in which all of the walls are of the same relative thickness.

The outer margins of the sample or support plate 10 may lie on the outer and uppermost margins of the sidewalls 27*a* and 27*b* and/or endwalls 28*a* and 28*b* of the lower compartment 7, or may be affixed, mounted or attached to the inner sidewalls 27*a* and 27*b* and endwalls 28*a* and 28*b* of the lower compartment 7 by, for example, a support bracket.

Figure 4:
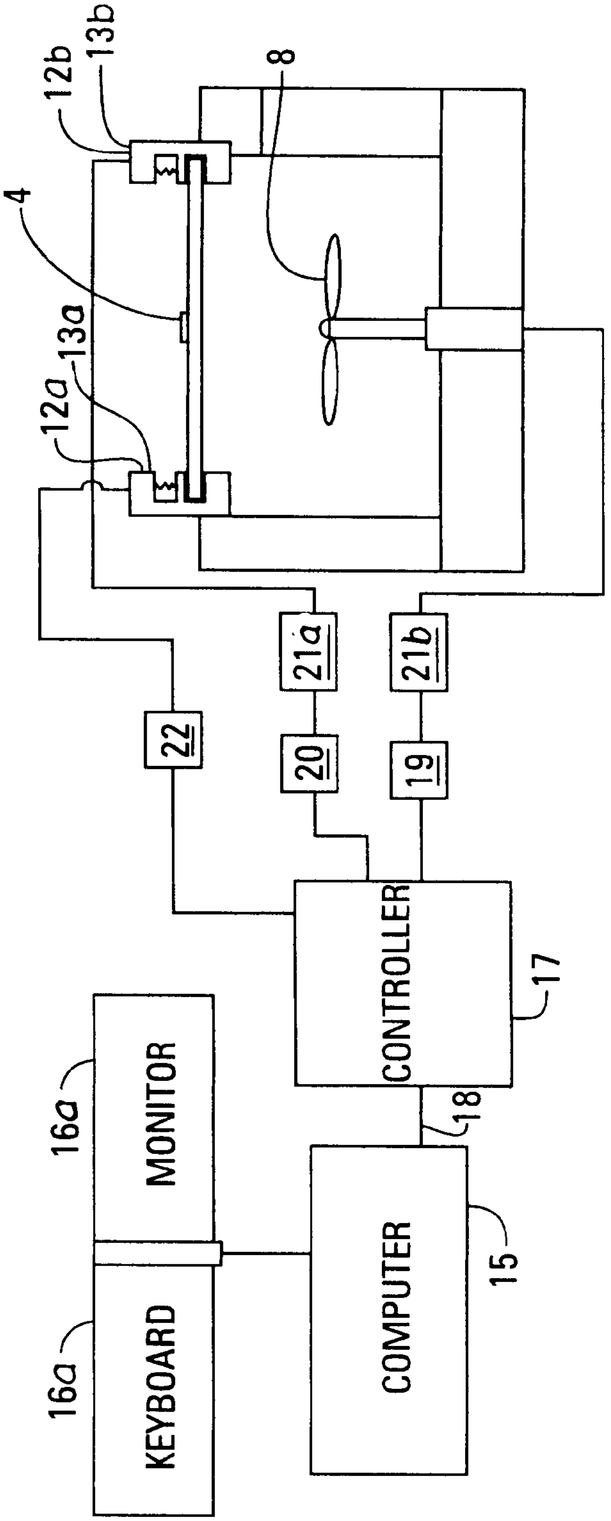
FIG. 4 is a block diagram of one embodiment of the invention.

FIG. 4 is a block diagram of one embodiment of the invention. A microcomputer 15 can be programmed by means of input keys 16*a* and monitor 16*b* to cause the microscope slide to be cycled through a series of temperatures over a period of time. It is contemplated that the device of the invention would include, as appropriate, timing mechanisms, electronic or otherwise, for maintaining time intervals for each cycle, and for counting the number of repetitions. The microcomputer is electronically attached to a temperature or process controller 17 by means of a communications cable 18. This controller regulates the supply of power 20 to the clips 12, and power 19 to the fan 8 by means of output relays 21*a* and 21*b*. It also contains an electronic sensing device, e.g., an analog to digital converter 22, that is connected to the temperature sensor 4.

Figure 5:
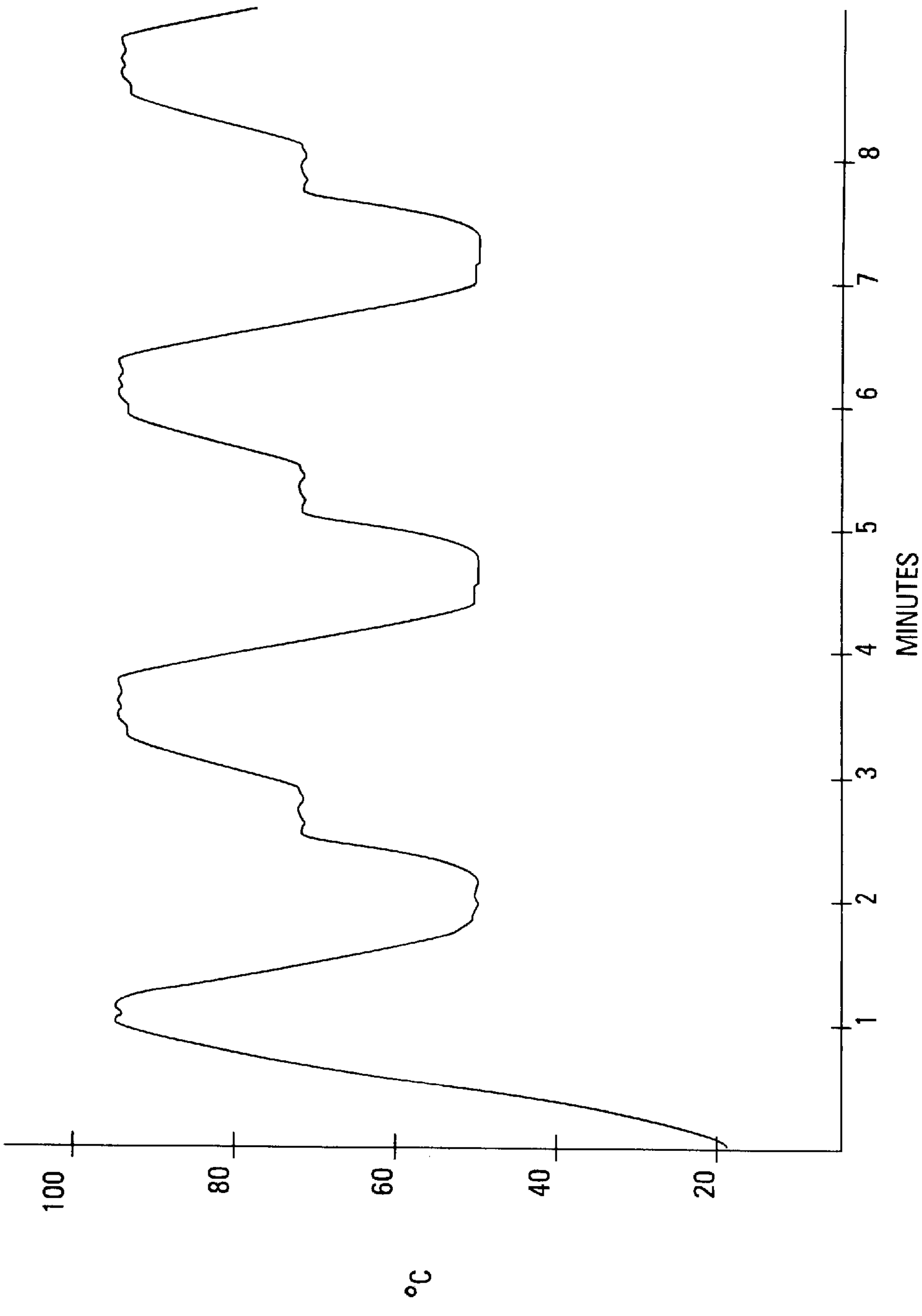
FIG. 5 illustrates the temperature profile of a microscope slide.

When the device of the present invention is used for cyclic DNA amplification, repetitive cycling through a temperature versus time profile is required. Samples containing a reaction mixture for the polymerase chain reaction generally must be cycled approximately 30–40 times through a temperature versus time profile which corresponds to the denaturation, annealing and elongation phases of the amplification process. FIG. 5 illustrates, in graphic form, the temperature profile of a microscope slide undergoing thermal cycling. FIG. 5 illustrates the temperature profile of a microscope slide with a 5.5Ω platinum heater, provided with 10 V alternating current, and slide temperature monitored by a 100Ω platinum RTD. The slide was repeatedly cycled through temperatures of 94° C., 50° C., and 72° C., with 20 second incubations at each temperature. The slide was heated at an average rate of 1.2° C. per second, and cooled at an average rate of 1.1° C. per second.

Thus, as a result of use of the present invention, it is possible to realize temperature increases of the flat substrate of at least about 1.0° C./second, more preferably at least about 1.5° C./second, and even more preferably at least about 2.0° C./second, or greater, and temperature decreases of the flat substrate of at least about 0.5° C./second, preferably at least about 1.0° C./second, and more preferably at least about 1.5° C./second or greater. Also it is preferred that the spatial temperature variation on the substrate and/or biological sample is less than about 0.5° C., and more preferably less than about 0.1° C.

The invention also provides a thermal cycler comprising a silicon sample plate which is optimized for heat flow to and from biological samples attached or affixed to a flat substrate, e.g., a microscope slide, present on the upper surface of the sample plate. For in situ PCR applications where very few slides are to be run simultaneously, the top surface is designed to create flat horizontal areas large enough to hold slides so that the large dimensions (height and width) are horizontal. These flat areas may be recessed in shallow wells, which may optionally hold a vapor barrier that covers the slides, or which physically isolate one substrate from another. For microscope slides, the area is at least about 16 mm wide and 77 mm long to fit conventional glass microscope slides. The wells are at least about 2 mm deep to fit a slide and cover slip and optionally a vapor barrier.

For in situ PCR applications where a large number of samples each affixed to a flat substrate such as a microscope slide are to be run simultaneously, the silicon sample plate may be designed to contain many narrow, deep, vertical or approximately vertical slots, sized to hold slides inserted edgewise with minimal space separating the slide from the silicon surfaces facing the top and bottom surfaces of the slide. The intervening space normally is filled with mineral oil or another nonvolatile liquid to provide a vapor barrier and efficient heat transfer during thermal cycling. However, because the heat transfer between a flat sample plate and a flat substrate is more efficient, a vapor barrier may be optional for some applications. The plane of a slot may be inclined from the vertical by as much as about 45° in order to use the force of gravity to assure that one surface of the slide touches the silicon of the sample plate. Slots must be about 15 mm deep, at least 77 mm long, and at least 2 mm wide to fit a conventional slide plus a cover slip. This design is not compatible with manual addition of missing PCR reagent(s) because it blocks rapid access to the in situ PCR preparation for cover slip removal, manual addition of the missing PCR reagent(s), and cover slip replacement.

It is also envisioned that the silicon sample plate of the invention may be prepared so as to replace the top surface of a sample plate present in a commercially available thermal cycler, leaving the other design features (except possibly plate or block thickness) unchanged in order to minimize the impact of the invention on thermal cycler manufacture and performance. It is also envisioned that the silicon sample plate of the invention is equal in mass to the conventional sample block of a commercially available thermal cycler, to minimize impact on heating and cooling kinetics.

The device of the invention 54 is preferably enclosed in a housing or body which comprises a lower hollow compartment 40 and an upper hollow compartment (39). Although the two compartments 39 and 40 may be formed in any suitable, compatible and practical shape, they are preferably box-shaped. Each compartment comprises a pair of sidewalls 34*a* and 34*b* and a pair of endwalls 35*a* and 35*b*. The lid also comprises a flat upper surface 31 attached to the sidewalls and endwalls of the lid. The lower compartment 40 comprises a flat lower surface the outer surface on which, preferably, are feet. The lower surface comprises an inlet opening 43 for ambient air intake. The lower surface 30 of the lower compartment is attached to the sidewalls 34*a* and 34*b* and endwalls 35*a* and 35*b* of the lower compartment 40. The sidewalls 34*a* and 34*b* and/or endwalls 35*a* and 35*b* of the lower compartment 40 have at least one outlet opening 41.

The housing may be fabricated from any available material, e.g., a plastic, metal, such as stainless steel, silicon, glass or combinations of any of the foregoing materials. However, it is preferred that the material be plastic, such as polypropylene or polycarbonate or the like, so that the housing may be molded in an inexpensive fashion. Moreover, it is preferred that the walls of the housing, including sidewalls 34*a* and 34*b*, endwalls 35*a* and 35*b*, lower surface, and upper surface, be relatively thin in dimension in order to provide a housing with low thermal mass. The most straightforward, but not necessarily limitative, construction of housing is one in which all of the walls are of the same relative thickness.

The lower compartment 40 comprises a silicon sample plate 32, which provides mechanical support and a heat exchange element for the flat substrates. The outer margins of the sample plate and may lie on the outer and uppermost margins of the lower compartment 40, or may be affixed, mounted or attached to the inner sidewalls 34*a* and 34*b* and endwalls 35*a* and 35*b* of the lower compartment 40 by, for example, a support bracket. The silicon sample plate 32 may be flat, or may comprise a plurality of recessed rectilinear wells for microscope slides. It is preferred that the wells in the sample plate may include sidewalls which are integrally formed in, and from the same material as, the silicon sample plate 32. Moreover, the wells are preferably configured to hold the slides, or other flat substrate, in relatively tight contact with sidewalls of the wells, to facilitate optimum conduction of heat to and from the slides.

Figure 6:
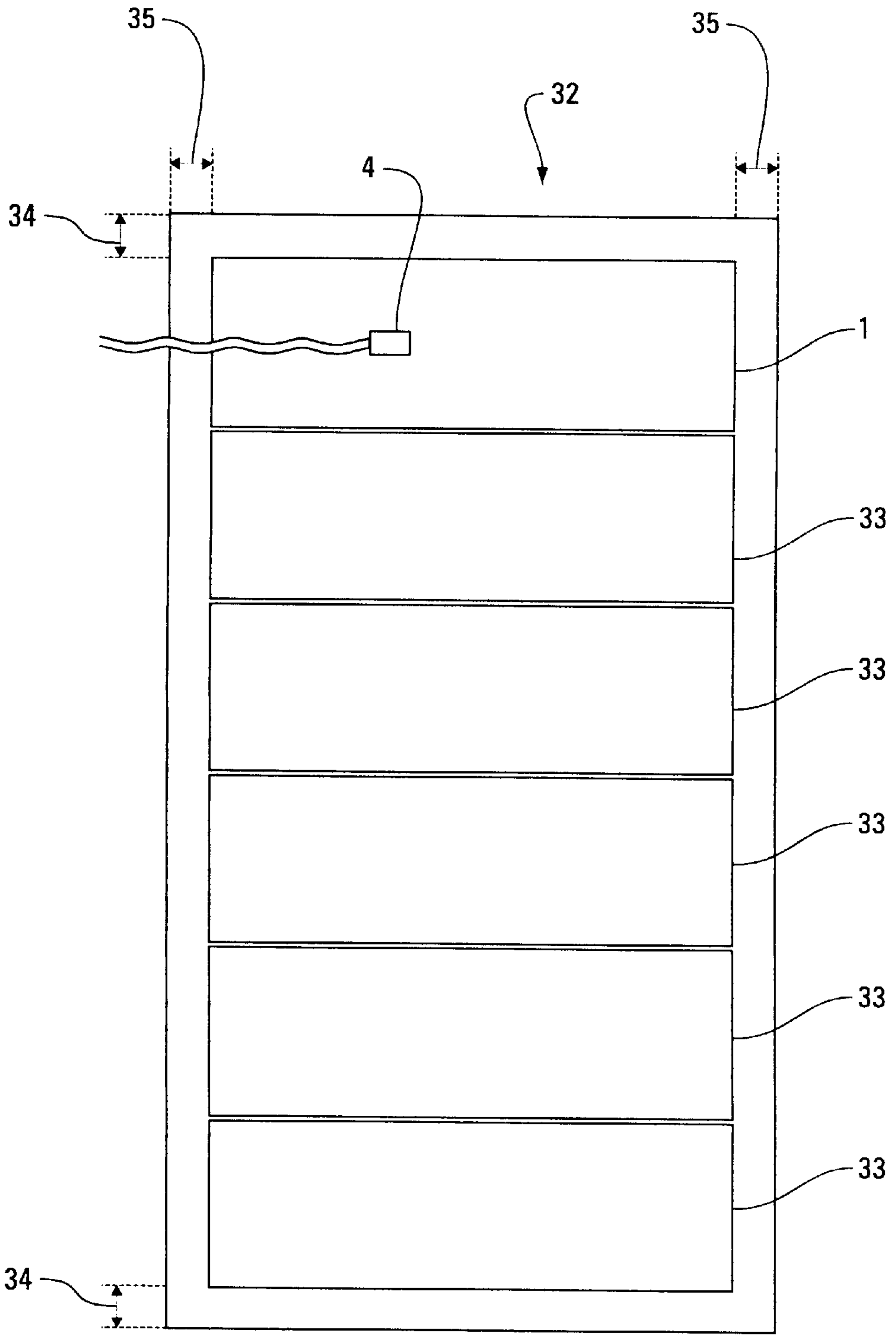
FIG. 6 is a top view of a preferred embodiment of a silicon sample plate having microscope slides, at least one of which is fitted with a temperature sensor.

Reference is now made to the drawings, which describe preferred embodiments of the invention, but are not intended to limit the invention to the embodiments shown. FIG. 6 is a top view of a rectilinear silicon sample plate 32, a microscope slide 1 fitted with a temperature sensor 4, and an array of experimental slides 33. The endwall margins 34 and the sidewall margins 35 of the sample plate provide support for a lid, which covers the sample plate 32 and slides. In this embodiment, the silicon sample plate 32 is 6.5" long and 3.5" wide. Since standard microscope slides are 3" long and 1" wide, the illustrated sample plate accommodates the slide with a temperature sensor 4, and five experimental slides 33. As shown in FIG. 6, a silicon sample plate 32, is dimensioned so as to accommodate 6 microscope slides. However, the silicon sample plate may be fashioned so as to accommodate fewer or greater than 6 flat substrates. The upper surface of one representative flat substrate, e.g., a microscope slide, is attached to a thermosensor 4. The other flat substrates each comprise at least one biological sample on their upper surface. The outer edges or margins of the surface of the silicon sample plate 34 and 35 are useful for placing the lower edges of a lid over the slides during thermal cycling.

The thermosensor 4 is an integrated circuit which provides an output current that is directly proportional to temperature (K°) (AD592 or AD590 from Analog Devices, Norwood, Mass.). The thermosensor 4 thus provides an electrical input signal to the microcomputer or microprocessor 46 which corresponds to the temperature of the representative flat substrate on the sample plate 32. Temperature monitoring during operation of the thermal cycling device of the present invention is preferably achieved using a type K thermocouple (COI-K; Omega Engineering, Inc., Stamford, Conn.) or a 100Ω resistance temperature device F3101; Omega Engineering, Inc., Stamford, Conn.). The controller uses this information to regulate the heating means and cooling means according to redetermined temperature versus time profiles programmed therein.

Figure 7:
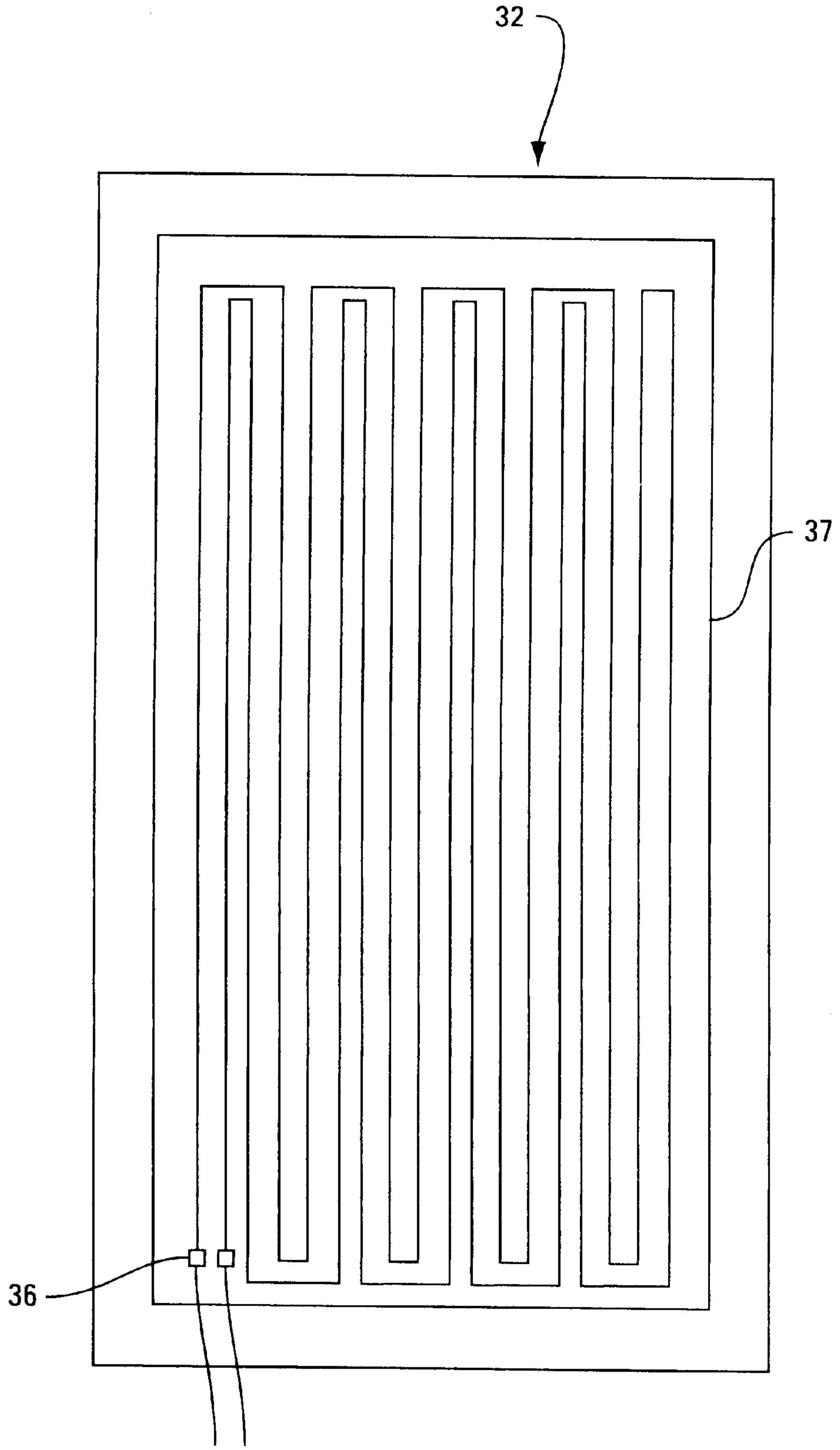
FIG. 7 is a bottom view of the silicon sample plate.

FIG. 7 is a bottom view of the silicon sample plate 32 to which a 6" long×3" heater 37 is attached. A solder pad connection 36 is attached to the lower surface of the heater. An exemplary heating means 37 is preferably an etched foil type heater (HK 5468 R93.8 L12A; MINCO Products, Minneapolis, Minn.) which is preferably glued to the silicon sample plate 32. However, any heating unit suitable for heating the silicon sample plate may be used. The heating means is activated by an output relay attached to the microcomputer or microprocessor 46. Preferably, the relay is Crydom A1202 purchased from Allied Electronics, Fort Worth, Tex.).

Figure 8:
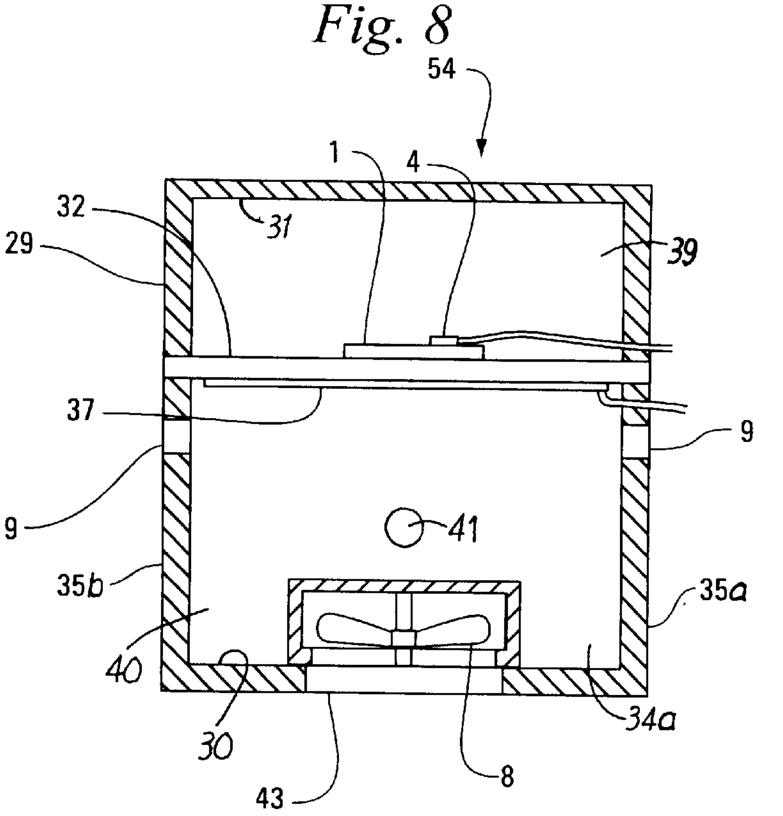
FIG. 8 illustrates a cross sectional view of a fan mounting arrangement in which the impeller blades of a fan are parallel to the silicon sample plate.

FIG. 8 illustrates a cross sectional view of a fan mounting arrangement in which the impeller blades of a fan 8 are parallel to the silicon sample plate 32. Also shown are the lid 29 and outlet openings or vents 9. The lid can be opened to allow access to the silicon sample plate 32. To cool the silicon sample plate 32, the heating means 37 is deactivated and the fan 8 is activated. Air from outside the housing is drawn into the lower compartment 40 though an inlet opening 43 by the fan 8 which is connected to a motor shaft driven by a motor (not shown). The fan 8 is mounted to the interior surface of the lower wall of the lower compartment, although other mounting arrangements are envisioned. The lower surface has a inlet opening 43. There is at least one other opening 9 in the sidewall 34*a* or 34*b* or the endwall 35*a* or 35*b* of the lower compartment 40. Hence, air is drawn into the lower compartment 40 through input openings or vents 43 and driven against the heater by the fan 8, and out of the lower compartment 40 through vents 9 in the endwalls 35*a* and 35*b* located perpendicular to and between the fan 8 and the heater 37. Thus, the present invention may have two such openings, but the present invention is not limited to two since the number of openings may vary, depending upon the design and configuration of the housing. These openings provide communication between interior of the housing and the outside environment, so that air may be moved into and out of the hollow interior of the lower compartment, according to the present invention.

The fan assembly preferably employs a propeller type fan due to its generally low thermal mass, or if desired, a squirrel cage type fan, the fan preferably having at least about 40, more preferably at least about 50, and even more preferably at least about 60 cubic feet per minute minimum capacity. The fan 8 draws ambient temperature air through the inlet opening 43 into the hollow interior of the lower compartment, and forces the air against the heating means 37. The air is dispersed through outlet or exit openings 9 in the endwall or sidewalls of the lower compartment. Operation of the fan 8 allows the sample plate 32 in to be brought to a lower predetermined temperature as quickly as possible. Thus, due to the minimum thermal mass of the sample plate 32, and the action of the fan 8, vast quantities of air are forced against the heating means 37 and from there out of the hollow interior of the outlet openings 9 in the lower compartment 40. Thus, rapid cooling of flat substrates on the sample plate is obtained. Moreover, the combination of heating and cooling means together allow the flat substrates to be maintained at a particular temperature.

The fan motor (not shown) is located externally of housing. It would be disadvantageous to mount the motor within the chamber which would subject the motor to temperature variations and also would add the thermal mass of the motor to that which is subject to heating and cooling. For example, a Comair FT12M3 fan purchased from Digi-Key Corporation (Thief River Falls, Minn.;) can be employed in the device of the invention, although other cooling devices and fans well known to the art may be employed in the practice of the invention.

Figure 9:
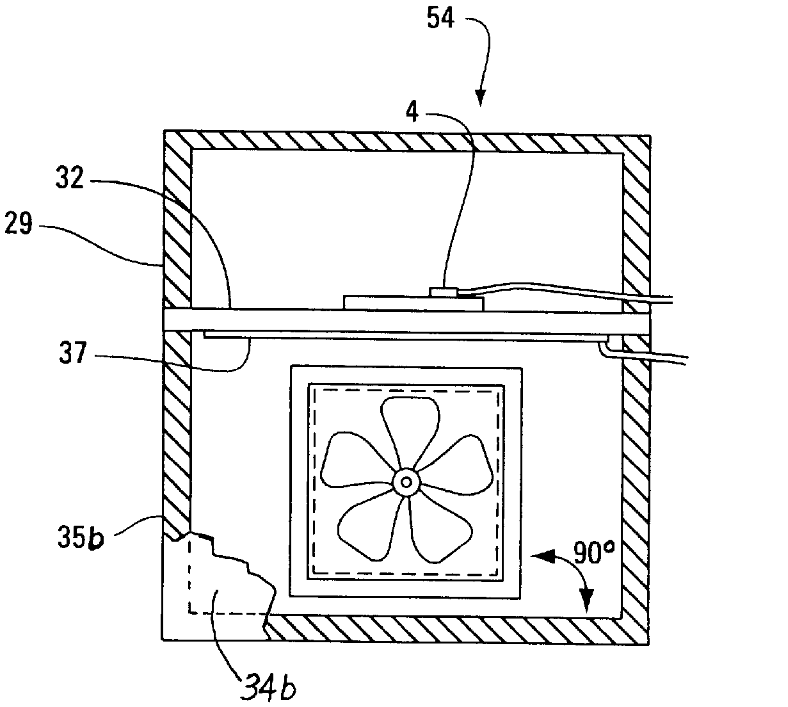
FIG. 9 illustrates a fan mounting arrangement in which the impeller blades of the fan are at an angle, i.e., perpendicular, to the silicon sample plate.

FIG. 9 illustrates a fan mounting arrangement in which the impeller blades of the fan 8 are at an angle, i.e., perpendicular, to the silicon sample plate 32. Air is drawn into the lower compartment, diverted 90°, driven against the heater, and out of the lower compartment through vents (not shown) on the sidewalls.

Figure 10:
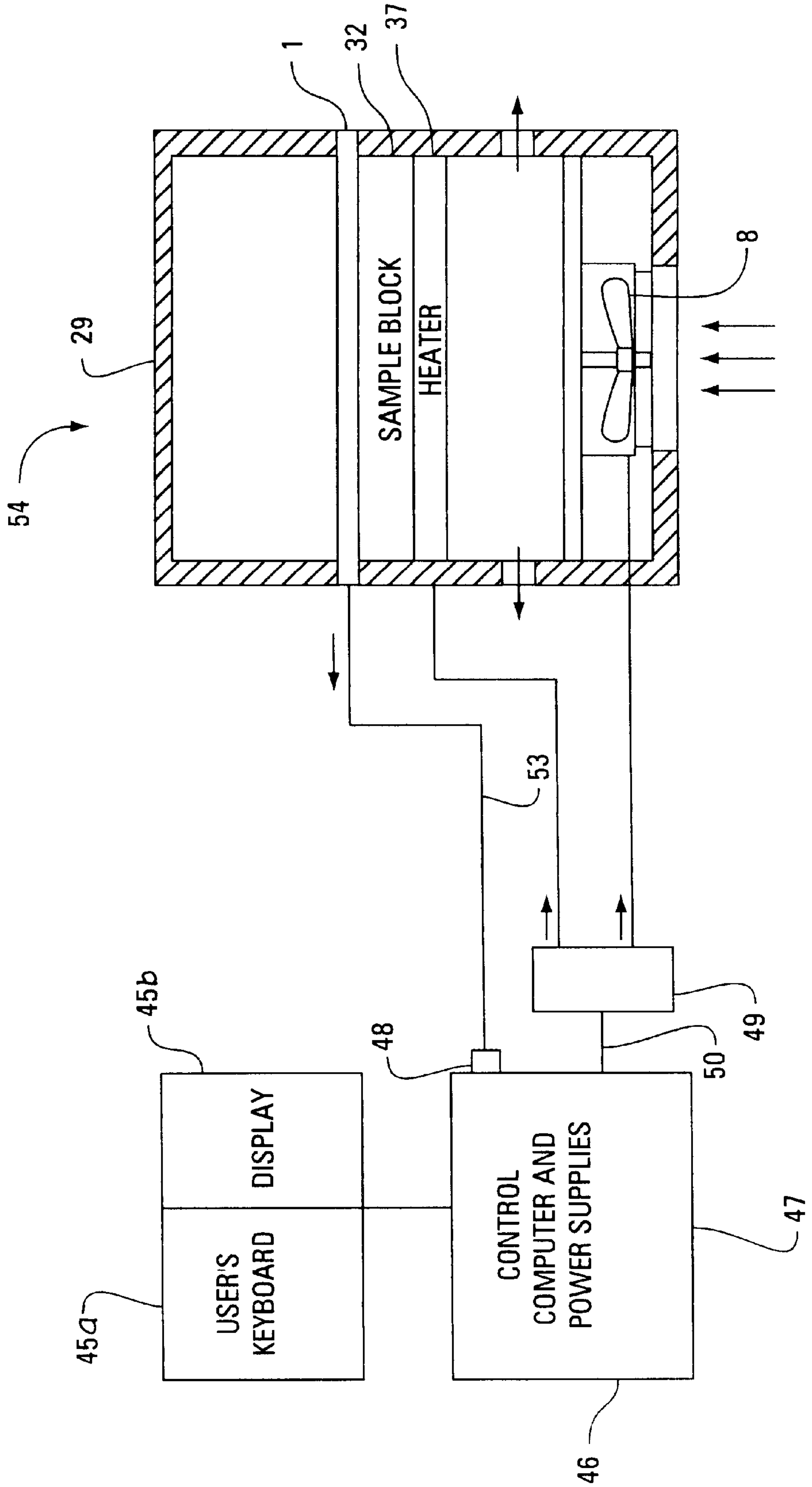
FIG. 10 is a block diagram of the thermal cycler of the invention.

FIG. 10 is a block diagram of the thermal cycler of the invention. Shown are the thermal cycling device 54, a user's keyboard and display 45*a* and 45*b*, and a computer 46/power supply 47. Also shown are an analog to digital converter 48, a cable 50 and a connector 53. A microcomputer or microprocessor 46 can be programmed by means of input keys 45*a* and display 45*b* to cause the flat substrate on the silicon sample plate 32 to be cycled through a series of temperatures over a predetermined period of time. Although not specifically illustrated in the drawings, it is contemplated that the device of the invention would include, as appropriate, timing mechanisms, electronic or otherwise, for maintaining time intervals for each cycle, and for counting the number of repetitions.

The microcomputer or microprocessor 46 is electrically attached to a relay controller 49 by means of a transmission cable 50. This controller 49 regulates the supply of power 46 to the heating means 37. It also regulates the supply of power to the fan blower motor (not shown). A preferred controller is available from JBR Electronic Systems, Inc. (Baltimore, Md.; ECP2). The cable also supplies power to the blower motor (not shown), and to the heating means 37.

The microcomputer or microprocessor 46 also is connected to an electronic sensing device which is an analog to digital converter 48 that is connected to the temperature sensor. A preferred converter 48 is the DAS-TEMP, available from Keithley Metrabyte (Taunton, Mass.). The microcomputer or microprocessor 46 can be any well-known type of temperature controller unit which is programmable to control the heating means 37 and fan motor so as to achieve predetermined temperatures as a function of time on the flat substrates present on the silicon sample plate 32.

When the device of the present invention is used for cyclic DNA amplification, repetitive cycling through a temperature versus time profile is required. Samples containing a reaction mixture for the polymerase chain reaction generally must be cycled approximately 30–40 times through a temperature versus time profile which corresponds to the denaturation, annealing and elongation phases of the amplification process.

Method of the Invention

To amplify nucleic acid sequences in a biological sample, such as a histochemical section or cytochemical smear attached to a microscope slide, the section or smear on the microscope slide is preferably covered with about 5 to 25 μl, more preferably about 5 to 10 μl, of a PCR reagent mixture. Preferably, the PCR reagent mixture lacks at least one reagent, such as enzyme. Then a plastic cover slip is placed over the preparation, the microscope slide is placed in a thermal cycler. After the sample is brought to about 80° C. and held at that temperature, the cover slip is lifted and 2 to 10 $\mu$l of PCR buffer containing the missing reagent(s) are distributed across the surface of the reagent mixture. The cover slip is replaced, and the slide is covered with enough mineral oil to assure that the cover slip, including their edges, is protected from the atmosphere. Preferably, the oil has been pre-heated, so that its addition does not transiently reduce the temperature of the in situ PCR preparation. Then a standard two-temperature or three-temperature thermal cycle is run for about 40 cycles. Cycle parameters, e.g., number of cycles, and PCR reagent concentrations are optimized by methods well known to the art.

After amplification, the mineral oil is removed from the slide with an organic solvent such as xylene, and the slides are dried with 100% ethanol or a graded series of ethanol concentrations. The oil-free preparation is incubated for approximately 15 minutes at about 50° C. in 0.15 M NaCl, 0.015 M Na citrate, pH 7.0 to remove unreacted PCR reagents.

The detection phase of in situ PCR employs two basic detection strategies. The first strategy involves tagging either the PCR primers or at least one of the dNTPs with a radioisotope or with a binding moiety such as biotin, digoxigenin, or fluorescein, or with another fluorophore. In this case, tag incorporated into amplified nucleic acid can be analyzed directly, provided that the unreacted tagged reagent has been washed out post-PCR and provided that the washing and drying procedure has not mobilized the amplified nucleic acid from its point of synthesis. The analytical validity of this simple detection strategy requires that the invention has increased in situ PCR specificity sufficiently that negligible nonspecific products have been made which are large enough to resist washing from the preparation.

To test and validate this consequence, appropriate control reactions can be performed. The logically most compelling control reaction is to perform the procedure on cells known to lack the target sequence; validation of the simplified detection strategy requires that no signal be generated in the control cells. Often such control cells are present in a histochemical or cytochemical preparation, so that the standard analysis contains its own control. A less compelling control is to use primers which differ sufficiently from the optimal primers for the target sequence that they will not amplify the target sequence under the specified annealing and extension conditions.

To detect amplified nucleic acid by in situ hybridization to a tagged nucleic acid probe, an oligonucleotide or polynucleotide with a sequence complementary to at least part of the amplified nucleic acid sequences (preferably excluding the primer sequences) is employed. In situ hybridization, well known in the histochemical and cytochemical art, has four basic steps: denaturation of DNA in the test sample, annealing of probe to test sample nucleic acid under stringent conditions, wash of the microscope slide with a solvent under stringent conditions to remove unhybridized probe, and detection of the probe which has been retained on the slide.

Regardless of which detection strategy is used, the methods for observing and recording the presence and location of tag on the microscope slide are the same. If the tag is a radioisotope (preferably a strong beta radiation-emitter, such as $^{32}$P or $^{125}$I), the microscope slide is coated with nuclear track emulsion such as NTB-2 from Eastman Kodak Co. (Rochester, N.Y.), incubated at 4° C. for an interval determined by trial and error, and developed by standard methods to leave microscopically detectable silver grains in the vicinity of immobilized tags. Procedures for $^{125}$I tagging probe or PCR product are described by Haase et al., *Proc. Natl. Acad. Sci USA,* 87, 4971 (1990), incorporated herein by reference.

If the tag is a fluorophore, it may be observed directly in a fluorescence microscope with excitation and emission filters optimized for the particular fluorophore. This detection method is particularly suitable for multiplex in situ PCR with different primer pairs for different target nucleic acid sequences. Either different fluorophores can be attached to primers of different specificity, or different fluorophores can be attached to probes of different specificity. Methods of attaching fluorophores to oligonucleotides and polynucleotides, preferably at their 5' ends, are well known in the nucleic acid chemistry and PCR arts.

If the tag is a binding moiety such as biotin or digoxigenin, it is incorporated directly into PCR product (via primers or dNTPs) or into probes by essentially the same methods used to attach other tags. However, in this case, signal generation requires additional detection steps.

Preferably, the microscope slide is incubated in buffered aqueous solvent containing a covalent conjugate of a detection enzyme and a binding protein specific for the tag (avidin or streptavidin for biotin, an anti-digoxigenin antibody for digoxigenin, an anti-fluorescein antibody for fluorescein). The preferred detection enzyme is horseradish peroxidase or alkaline phosphatase. After unbound enzyme conjugate is removed by washing in a buffered aqueous solvent, the microscope slide is immersed in a solution containing a chromogenic substrate for the enzyme used. After an insoluble dye, product of the enzyme reaction, has been deposited at points on the microscope slide where enzyme conjugate has been bound, unreacted substrate is washed away in water or buffered aqueous solvent to prevent the buildup of nonspecific background stain over time. The preferred chromogenic substrates which generate insoluble products are well known in the histochemical and cytochemical art, as are the methods for staining and for enzyme conjugate incubation and washing. The substrates and enzyme conjugates are commercially available from a wide variety of sources well known to histochemists and cytochemists.

A preferred companion procedure in the detection steps of the present invention is counterstaining of the microscope slide with fluorescent dyes (for fluorescent tags) or chromophoric dyes (for radio-autoradiographic detection or enzymatic generation of insoluble chromophores) which emit or absorb with different spectral characteristics than the analyze-specific signals and which highlight cell structures, especially in cells which lack target nucleic acid sequence. Especially preferred for examination of insoluble blue dye deposits by transmission microscopy is counterstaining by nuclear fast red, standard in the histochemical and cytochemical art. The methods for examining stained in situ PCR preparations by transmission or fluorescence microscopy are well known in the histochemical and cytochemical art, as are methods of recording permanently the microscopic image photographically or via digitized video images.

The invention will be further described by the following non-limiting examples.

EXAMPLE 1

FIG. 1 depicts a preferred apparatus of the invention, which comprises a microscope slide 1, a thin-film heater 2, and a thin-film resistive temperature-monitoring device 4. The heater 2 is associated with conductive pads 3*a* and 3*b*, at opposite ends of the edge of the slide, preferably at the ends of the edges which are farthest apart. The temperature-monitoring device 4 is associated with conductive pads 5*a* and 5*b* at the ends of the edges of the slide, preferably at the ends of the edges which are closest in proximity. Preferably, the apparatus comprises a light-transparent heater on the lower surface of the microscope slide and a temperature-monitoring device on the upper surface of the microscope slide, although the heater may be associated with the upper surface of the slide and the temperature-monitoring device associated with the lower surface. The microscope slides are about 3.0" long, about 1.0" wide, and about 0.125" thick. The heating element is preferably a microfabricated heater.

Such an apparatus may be placed in a thermal cycling device of the invention. See, for example, FIGS. 2, 3 and 4. FIG. 2 shows a side view of a device of the invention. Conductive clips 12 and 13 are associated with a sample holder 10 which forms the top wall of the housing 6. The sample holder has an opening or gap 11 for the apparatus. The housing also includes a pair of endwalls 28 and/or side walls 27, as well as a bottom wall 30. A fan 8 is associated with the bottom wall 30. A lid 29, if present, can be opened to allow access to the slide.

In FIG. 3, a slide 1 is connected to a conductive clip 12 associated with the housing of a thermal cycling device of the invention (see FIG. 4) or attached to a sample plate 10 (see FIG. 2) for use in a device of the invention. The opening 11 between the slide 1 and the plate 10 provides a vent.

FIG. 4 is a block diagram of the invention. A microcomputer or microprocessor 15 can be programmed by means of input keys 16*a* and display 16*b* to cause the flat substrate to be cycled through a series of temperatures over a predetermined period of time. Although not specifically illustrated in the drawings, it is contemplated that the device of the invention would include, as appropriate, timing mechanisms, electronic or otherwise, for maintaining time intervals for each cycle, and for counting the number of repetitions.

The microcomputer or microprocessor 15 is electrically attached to a controller 17 by means of a cable 18. This controller 17 regulates the supply of power 20 to the heating element 2 via a conductive clip 12. It also regulates the supply of power 19 to the fan 8. A preferred controller is available from Watlow Engineering (St. Louis, Mo.; model 982). The computer or controller 15 can be a commercial microcomputer or a self-contained microprocessor. A microprocessor can be incorporated into the control electronics of the device by methods well known to the art. The microprocessor executes commands written in software that collect user input via the keyboard, compare the input to actual temperatures, and turn off or on the heating 2 or cooling 8 units as appropriate. The electronics may also include a timer, readable by the microprocessor. This allows the microprocessor to compare the elapsed time that the flat substrate has been at a particular temperature and compare it to a desired time input by the user. The microcomputer or microprocessor 15 can be any well-known type of temperature controller unit which is programmable to control the heating element 2 and the fan 8 so as to achieve predetermined temperatures as a function of time on the flat substrate 1.

The controller 17 is also connected to an electronic sensing device which is an analog to digital converter 22 that is connected to the temperature-monitoring device 4. This device 22 takes the electrical signal produced by the temperature sensing device and converts it to a form that the circuitry of the computer can evaluate. Different types of temperature sensors require different specialized types of analog to digital converters. The computer program, implemented in a combination of assembly language and the C language, although other programming languages may be used, causes the computer 15 to evaluate the temperature received from the temperature sensing device 4, compare this value to the "target" temperature, and send appropriate electrical signals to the relays controlling the heater 2 and the fan 8. The relays can be of the solid state or mechanical varieties. Communication between the computer 15 and the relays is maintained by switching devices. These devices respond to signals from the computer by producing an altered electrical signal that causes a response in the relay. Specific patterns of signals from computer 15 to relays provide the means by which the substrate is heated, cooled, or maintained at a steady temperature.

The use of the apparatus of the invention with a device of the invention permits the direct measurement and regulation of the temperature of at least one slide comprising a biological sample placed in the thermal cycling device of the invention. The elimination of an external heat sink in the device facilitates heat transfer and so provides the basis for a thermal cycling device for microscope slides that outperforms currently employed thermal cycling devices. A preferred thermal cycler of the invention of one embodiment of the invention may include the following components. The device of the invention preferably comprises a housing comprising two sidewalls, two endwalls, a bottom wall, and optionally a lid (upper wall). If the device comprises a lid, the lid, the sample plate, side walls, end walls, and bottom wall form two hollow enclosures, an upper enclosure and a lower enclosure. The housing preferably is formed from polystyrene, polypropylene, polyethylene or other plastics with compatible electrical and thermal conductances. A sample plate, which may be fixed to the housing or may be removable, is parallel to the bottom wall and at a right angle to the sidewalls and endwalls. Alternatively, a sample plate may form the upper wall of the housing, yielding a device with a single hollow enclosure. The lower hollow enclosure contains a cooling means. The cooling means can be any propeller-type fan or "squirrel cage" fan, or thermoelectric cooling device. A preferred propeller-type fan is Acme AM4670, purchased from McMaster-Carr, Chicago, Ill. The fan 8 may be powered by alternating current or direct current. The impeller blades of the fan may be constructed from plastic or metal.

The heating element is activated by an output relay 21 attached to the conductive clips 12 and the microcomputer or microprocessor 15. Preferably, the relay is Crydom A1202 purchased from Allied Electronics, Fort Worth, Tex. The heating element is preferably microfabricated from indium tin oxide or platinum or other electrically resistive metals including indium tin oxide or other conducting oxide films that permit light transmission. Metals such as platinum, aluminum, nickel, nichrome, gold and the like may be employed to prepare a heating element. To prepare a light transparent heating element, thin films comprising the exemplary metals are preferably of a thickness of 400 angstroms or less. The heater's path and contours, intended to maintain uniform temperature over the surface of the slide as it is thermally cycled, can be determined by finite element thermal analysis, a computer-modeling method (ANSYS Inc., ANSYS5.51, ISO9001, UP 19981001, USA, 1994; Reddy et al., "Finite Element Analysis for Engineering Design", eds.; New York: Springer-Verlag, 1988. Arik et. al., "Development of CAD Model MEMS Micropumps", Modeling and Simulation of Microsystems, Puerto Rico, 1999; Zienkiewicz et al., "The Finite Element Method", McGraw-Hill Int. Editions, New York, 1991). A preferred embodiment of an apparatus of the invention apparatus of the invention comprises a heating element formed of indium tin oxide, e.g., of less than about 5,000 Å thick, or platinum, e.g., of less than 400 Å thick, preferably with an internal resistance of 5–6Ω.

The temperature-monitoring element is preferably microfabricated from metals or semiconductors that display a temperature-proportional change in resistance, voltage, or current. A preferred temperature-monitoring element for use in an apparatus of the invention is a 100Ω platinum resistance temperature device (RTD), which is capable of resolving temperature to 0.1° C.

To cool the slide 1, the heating element 2 is deactivated and the fan 8 is activated. Air from outside the housing is drawn into the lower compartment 7 though an inlet opening 9 by the fan 8 which is connected to a motor shaft driven by a motor. The present invention may have more than one opening, but the present invention is not limited to one since the number of openings may vary, depending upon the design and configuration of the housing. These openings provide communication between interior of the housing and the outside environment, so that air may be moved into and out of the hollow interior of the lower compartment, according to the present invention. The fan 8 is mounted to the interior surface of the lower wall of the lower compartment, although other mounting arrangements are envisioned.

The fan assembly preferably employs a propeller type fan due to its generally low thermal mass, or if desired, a squirrel cage type fan, the fan preferably having at least about 40, more preferably at least about 50, and even more preferably at least about 60 cubic feet per minute minimum capacity. The fan 8 draws ambient temperature air through the inlet opening 9 into the hollow interior of the lower compartment, and forces the air against the slide 1. The air is dispersed through outlet or exit openings in the endwall or sidewalls of the upper compartment, if present. Operation of the fan 8 allows the slide 1 in to be brought to a lower predetermined temperature as quickly as possible. Thus, due to the action of the fan 8, vast quantities of air are forced against the slide 1 and from there out of the hollow interior of the outlet openings in the upper compartment 24 or through the vents 11. Thus, rapid cooling of flat substrates is obtained. Moreover, the combination of heating and cooling means together allow the substrate to be maintained at a particular temperature.

The fan motor may be located externally of housing. It would be disadvantageous to mount the motor within the chamber which would subject the motor to temperature variations and also would add the thermal mass of the motor to that which is subject to heating and cooling. For example, a Comair FT12M3 fan purchased from Digi-Key Corporation (Thief River Falls, Minn.;) can be employed in the device of the invention, although other cooling devices and fans well known to the art may be employed in the practice of the invention.

EXAMPLE 2

A thermal cycler of the invention 54 may include the following components. The housing, comprising a lid and a lower hollow compartment 40, is constructed from polystyrene, polypropylene, polyethylene or other plastics having appropriate thermal and electrical conductances. The silicon plate 32 is about 6.5" long, about 3.5" wide, and about 0.025" thick. The microscope slides are about 3.0" long, about 1.0" wide, and about 0.125" thick. The heater 37 is of the etched foil type, and is electrically insulated with a thin film of Kapton or similar substance. The fan 8 may be powered by alternating current or direct current. The impeller blades of the fan may be constructed from plastic or metal. The fan 8 and the heater 37 are controlled by electrical switches of the relay type. The relays can be of the solid state or mechanical varieties.

The computer or controller can be a commercial microcomputer or a self-contained microprocessor. A microprocessor can be incorporated into the control electronics of the apparatus by methods well known to the art. The microprocessor executes commands written in software that collect user input via the keyboard, compare the input to actual temperatures, and turn off or on the heating or cooling units as appropriate. The electronics may also include a timer, readable by the microprocessor. This allows the microprocessor to compare the elapsed time that the reaction mixture has been at a particular temperature and compare it to a desired time input by the user.

The temperature sensor can be of the thermocouple type, or the thermistor type, or the resistance temperature detector type, or the current detector type. In each of these devices, a change in temperature at the interface between the sensor and its environment produces a change in the ability of the sensor to conduct electrical current. The sensors generate electrical signals that are proportional to the extent of the temperature change. The temperatures of the experimental slides are taken by the thermosensor as the temperature of the representative slide. The difference between the rates of active and passive convection illustrates that a cooling means, e.g., a fan, is required for the effective performance of the invention.

Communication between the computer and the temperature sensor is maintained by an electrical device known as an analog to digital converter. This device takes the electrical signal produced by the temperature sensor and converts it to a form that the circuitry of the computer can evaluate. Different types of temperature sensors require different specialized types of analog to digital converters.

Communication between the computer and the relays is maintained by switching devices. These devices respond to signals from the computer by producing an altered electrical signal that causes a response in the relay.

The computer program, implemented in a combination of assembly language and the C language, although other programming languages may be used, causes the computer to evaluate the temperature received from the temperature sensor, compare this value to the "target" temperature, and send appropriate electrical signals to the relays controlling the heater and the fan. Specific patterns of signals from computer to relays provide the means by which the representative slide is heated, cooled, or maintained at a steady temperature

EXAMPLE 3

Cells of the stable human cervical cancer cell line, SiHa (ATCC HTB 35), containing one integrated copy of human papilloma virus (HPB) type 16 genome per human genome, are grown to density of about $10^5$ cells/mL in Eagle's minimal essential medium with non-essential amino acids, sodium pyruvate, and 15% fetal bovine serum, washed two times in Tris-buffered saline, adjusted to an approximate density of $10^4$ cells/mL, and stirred overnight at room temperature in 10% (vol/vol) formaldehyde in phosphate buffer. The formaldehyde-fixed cells are centrifuged at 2,000 rpm for 3 minutes, and the pellet is embedded in paraffin. Microtome sections (4 μm thickness) of the paraffin block are attached to glass microscope slides which had been dipped in 2% 3-aminopropyltriethoxysilane (Aldrich Chemical Co.) in acetone by floating the sections in a water bath.

After attachment, sections are deparaffinized and proteolytically digested with reagents from the Viratype® in situ Tissue Hybridization Kit (Life Technologies, Inc., Gaithersburg, Md.) following the manufacturer's instructions. Slides are overlaid with 5 to 10 μl of PCR solution (see below). A plastic cover slip is placed over each in situ PCR preparation. The cover slip is anchored to the slide with a drop of nail polish. The slide is placed on the sample plate 7 of the thermal cycler described in Example 1, and covered with approximately 1 ml of mineral oil.

The pH 8.3 PCR solution contains 10 mM TrisCl, 50 mM KCl, 4.5 mM $MgCl_2$, 20 mM of each dNTP, 0.2 unit/μL of AmpliTaq® DNA polymerase (Perkin Elmer Cetus Instruments, Norwalk, Conn.), and 6 μM of each primer. The primers employed are PV1, PV2, PV3, PV4, PV5, PV6 and PV7 (see U.S. Pat. No. 5; PV1 5' CAGGACCCACAGGAGCGACC 3' (SEQ ID NO:1); PV2 5' TTACAGCTGGGTTTCTCTAC 3' (SEQ ID NO:2); PV3 5' CCGGTCG ATGTATGTCTTGT 3' (SEQ ID NO:3); PV4 5' ATCCCCTGTTTTTTTTTCCA 3' (SEQ ID NO:4); PV5 5' GGTACGGGATGTAATGGATG 3' (SEQ ID NO:5); PV6 5' CCACTTCCACCACTATACTG 3' (SEQ ID NO:6); PV7 5' AGGTAGAAGGGCGCCATGAG 3' (SEQ ID NO:7)) which result in the production of overlapping approximately 450 bp PCR products. The predicted PCR product is a 1247 bp product.

For the first thermal cycle, denaturation is performed for 3 minutes at 94° C., and annealing/extension are performed for 2 minutes at 55° C.; the remaining 39 cycles consist of 1 minute denaturation at 94° C. and 2 minutes annealing-extension.

After DNA amplification, mineral oil is removed by dipping in xylene, the cover slip is removed, and the mounted sections are dried in 100% ethanol. Each slide is incubated with 10 μl of a 500 ng/ml solution of biotinylated HPV type 16 specific polynucleotide probe (Viratype Kit, Life Technologies, Inc.) in 0.03 M Na citrate, 0.30 M NaCl, pH 7.0, 5% dextran sulfate, 50% formamide at 100° C. for 5 minutes and then 37° C. for 2 hours; then the slide is treated with an alkaline phosphatase-streptavidin conjugate and the phosphatase substrates, 5-bromo-4-chloro-3-indolyl phosphate (BCIP) and nitro blue tetrazolium (NBT), according to the instructions of the supplier of the S6800 Staining Kit (Oncor, Gaithersburg, Md.). After enzymatic detection of biotinylated probe captured on the sections, the sections are counterstained with nuclear fast red for 5 minutes.

When the stained slides are examined by transmission microscopy under 40–400 X magnification, single-copy HPV targets in SiHa cells are detectable in most nuclei.

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. An apparatus, comprising:

a slide having a first edge and a second edge opposite the first edge and at least a first pad and a second pad coupled therewith, the first pad disposed proximal to the first edge and the second pad disposed proximal to the second edge; and at least one resistive heating element associated with a lower surface of the slide and disposed alone a longitudinal axis of the slide, the heating element electrically coupled between the first pad and the second pad.

2. The apparatus of claim 1 which comprises a microscope slide.

3. The apparatus of claim 1 wherein the heating element is a thin-film heater.

4. The apparatus of claim 1 wherein the heating element is associated with a first horizontal surface of slide.

5. The apparatus of claim 1 wherein the heating element is transparent.

6. The apparatus of claim 5 wherein the heating element is light transparent.

7. The apparatus of claim 1 wherein the slide further comprises a third pad and a fourth pad coupled thereto.

8. The apparatus of claim 7 further comprising at least one temperature-monitoring element that is coupled between the third pad and the fourth pad.

9. The apparatus of claim 8 wherein the temperature-monitoring element is associated with a upper surface of the slide.

10. The apparatus of claim 8 further comprising a biological sample which comprises nucleic acid disposed on the slide.

11. The apparatus of claim 8 wherein the temperature-monitoring element is a thin-film resistive sensing element.

12. The apparatus of claim 1 or 6 wherein the heating element is formed of indium tin oxide.

13. The apparatus of claim 12 wherein the indium tin oxide is less than about 5,000 angstroms in thickness.

14. The apparatus of claim 1 or 6 wherein the heating element is formed of platinum.

15. The apparatus of claim 14 wherein the platinum is less than about 400 angstroms in thickness.

16. The apparatus of claim 8 wherein the temperature-monitoring element is a platinum resistance thermal sensing element.

17. The apparatus of claim 1 comprising at least two heating elements.

18. The apparatus of claim 8 comprising at least two temperature-monitoring elements.

19. A thermal cycling device, comprising:

a housing;

a cooling device associated with the housing, wherein the cooling device disperses air;

at least four conductive clips associated with the housing; and a controller, wherein the controller is operatively connected to each conductive clip and the cooling device.

20. The device of claim 19 further comprising a slide comprising at least one heating element and at least one temperature-monitoring element associated therewith.

21. The device of claim 20 wherein the slide is associated with the conductive clips.

22. The device of claim 20 further comprising a biological sample comprising nucleic acid, wherein the sample is disposed on the slide.

23. The device of claim 21 wherein two conductive clips are operatively connected to the heating element, and two other conductive clips are operatively connected to the temperature-monitoring element.

24. The device of claim 19 wherein the cooling device is a fan.

25. A device for thermal cycling, comprising:

a means for supporting at least one apparatus, wherein the apparatus comprises: i) a microscope slide having at least four pads coupled therewith, ii) at least one heating element associated with the slide, the heating element coupled between the first pad and the second pad, and iii) at least one temperature-monitoring element associated with the slide, the temperature-monitoring element coupled between the third and the fourth pads;

a means for cooling a surface of the microscope slide wherein the means for cooling comprises an air movement device; and a means for controlling a temperature of the microscope slide, wherein the means for controlling is operatively connected to the means for cooling, the heating element and the temperature-monitoring element such that the temperature of the slide can be rapidly and controllably increased and decreased by the controller in response to the temperature sensed by the temperature-monitoring element such that the apparatus can be subjected to rapid thermal cycling over a temperature range of at least 30° C.

26. The device of claim 25 wherein the means for cooling comprises a fan.

27. A device for subjecting a plurality of biological samples disposed on at least one flat substrate to thermal cycling, comprising:

a thermal sensing means placed on the surface of one flat substrate and at least one flat substrate lacking the thermal sensing means and comprising at least one biological sample;

a means for holding the plurality of flat substrates, wherein the means for holding comprises a silicon sample plate, and wherein the flat substrates are disposed on the surface of the holding means;

a means for heating the lower surface of the means for holding, wherein the means for heating is positioned in close proximity to the means for holding;

a means for cooling the surface of the means for heating, wherein the means for cooling comprises a rotating means for dispersing air; and a means for controlling, wherein the controlling means is operatively connected to the means for thermal sensing, the means for heating and the means for cooling such that the temperature of the substrates can be rapidly and controllably increased and decreased by the control means in response to the temperature sensed by the means for sensing such that the biological sample can be subjected to rapid thermal cycling over a temperature range of at least 40° C.

28. A device for maintaining the temperature of a plurality of biological samples which are disposed on at least one flat substrate, comprising:

a thermal sensing means placed on the surface of one flat substrate and at least one flat substrate lacking the thermal sensing means and comprising at least one biological sample;

a means for holding the plurality of flat substrates, wherein the means for holding comprises a silicon sample plate, and wherein the flat substrates are disposed on the surface of the holding means;

a means for heating the surface of the means for holding, wherein the means for heating is positioned in close proximity to the means for holding;

a means for cooling the surface of the means for heating, wherein the means for cooling comprises a rotating means for dispersing air; and a means for controlling, wherein the controlling means is operatively connected to the means for thermal sensing, the means for heating and the means for cooling such that the temperature of the substrates can be maintained at a particular temperature by the control means in response to the temperature sensed by the means for sensing such that the biological sample can be maintained at a particular temperature over a temperature range of at least 30° C.

29. The device of claim 27 or 28 wherein the means for sensing comprises a thermocouple.

30. The device of claim 27 or 28 wherein the means for sensing comprises a means other than a thermocouple.

31. The device of claim 27 or 28 wherein the flat substrate is a glass microscope slide.

32. The device of claim 27 or 28 wherein the heating means is an etched foil heater.

33. The device of claim 27 or 28 further comprising a housing containing the means for holding, the means for cooling, the means for heating, and the means for sensing.

34. A device for subjecting a biological sample to thermal cycling comprising:

a housing;

a flat substrate having a thermal sensor coupled to the flat substrate, the flat substrate having a biological sample disposed thereon;

a holder for the flat substrate, the holder attached to the housing, wherein the holder comprises a silicon sample plate, and wherein flat substrate is disposed on the surface of the silicon sample plate;

a cooler for the flat substrate, the cooler attached to the housing; and a heater thermally coupled to the holder.

35. The device of claim 34 wherein the holder holds a plurality of flat substrates.

36. The device of claim 34 the cooler is a fan.

37. The device of claim 34 wherein the heater is positioned in close proximity to the holder.

38. The device of claim 34 further comprising:

a controller operatively connected to the thermal sensor, the heater and the cooler such that the temperature of the flat substrate can be controllably increased and decreased by the controller in response to the temperature sensed by the means for thermal sensor.

39. The device of claim 34 wherein the biological sample can be subjected to rapid thermal cycling over a temperature range of at least 40° C.

* * * * *

UNITED STATES PATENT AND TRADEMARK OFFICE

CERTIFICATE OF CORRECTION

PATENT NO. : 6,300,124 B1
DATED : October 9, 2001
INVENTOR(S) : Gregory T. Cibuzar, Avram Bar-Cohen, Mehmet Arik, Martin Blumenfeld and Peter Schiller It is certified that error appears in the above-identified patent and that said Letters Patent is hereby corrected as shown below:

<u>Column 28,</u>
Line 9, please delete "alone" and insert -- along -- therefor.

<u>Column 30,</u>
Line 51, after "34" please insert -- wherein --.

Signed and Sealed this

Twenty-first Day of May, 2002

*Attest:*

JAMES E. ROGAN

*Attesting Officer*

*Director of the United States Patent and Trademark Office*